US011337617B2

United States Patent
Rundo et al.

(10) Patent No.: US 11,337,617 B2
(45) Date of Patent: May 24, 2022

(54) PROCESSING OF ELECTROPHYSIOLOGICAL SIGNALS

(71) Applicant: STMicroelectronics S.r.l., Agrate Brianza (IT)

(72) Inventors: Francesco Rundo, Gravina di Catania (IT); Piero Fallica, Catania (IT); Sabrina Conoci, Tremestieri Etneo (IT); Salvatore Petralia, Paterno (IT); Massimo Cataldo Mazzillo, Corato (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 880 days.

(21) Appl. No.: 16/037,328

(22) Filed: Jul. 17, 2018

(65) Prior Publication Data

US 2019/0021615 A1 Jan. 24, 2019

(30) Foreign Application Priority Data

Jul. 18, 2017 (IT) .................. 102017000081018

(51) Int. Cl.
*G06K 9/00* (2022.01)
*A61B 5/00* (2006.01)
(Continued)

(52) U.S. Cl.
CPC .......... *A61B 5/02416* (2013.01); *A61B 5/349* (2021.01); *A61B 5/725* (2013.01);
(Continued)

(58) Field of Classification Search
CPC ..... A61B 5/02416; A61B 5/349; A61B 5/725; A61B 5/7246; G16H 10/60; G16H 50/00;
(Continued)

(56) References Cited

U.S. PATENT DOCUMENTS

| 9,019,666 B2 | 4/2015 | Bourgeat et al. |
| 2011/0009754 A1* | 1/2011 | Wenzel ............... G03F 7/0002 600/485 |

(Continued)

FOREIGN PATENT DOCUMENTS

| WO | 2011089179 A1 | 7/2011 |
| WO | 2017089921 A1 | 6/2017 |

OTHER PUBLICATIONS

Vaz et al., An Automatic Method for Motion Artifacts Detection in Photoplethysmographic Signals Referenced With Electrocardiography Data, 2014 7th International Conference on BioMedical Engineering and Informatics, pp. 704-708. (Year: 2014).*

(Continued)

*Primary Examiner* — Jacqueline Cheng
*Assistant Examiner* — Tho Q Tran
(74) *Attorney, Agent, or Firm* — Slater Matsil, LLP

(57) ABSTRACT

In an embodiment, PhotoPlethysmoGraphy (PPG) signals are processed by detecting peaks and valleys in the PPG signal, segmenting the PPG signal to provide a time series of PPG waveforms located between two subsequent valleys in the PPG signal, applying to the waveforms in the time series pattern recognition with respect to a reference PPG waveform pattern produced based on a mathematical model of the PPG signal by assigning to the waveforms in the time series a recognition score. A resulting PPG signal is produced by retaining the waveforms in the time series having an assigned recognition score reaching a recognition threshold, and discarding the waveforms in the time series having an assigned recognition score failing to reach the recognition threshold.

22 Claims, 11 Drawing Sheets

(51) Int. Cl.
   G16H 10/60      (2018.01)
   A61B 5/349      (2021.01)
   A61B 5/024      (2006.01)
   G16H 50/00      (2018.01)
   G06V 40/10      (2022.01)

(52) U.S. Cl.
   CPC .......... *A61B 5/7246* (2013.01); *G06K 9/0053* (2013.01); *G06K 9/00503* (2013.01); *G16H 10/60* (2018.01); *G16H 50/00* (2018.01); *G06V 40/15* (2022.01)

(58) Field of Classification Search
   CPC ............. G06K 9/00503; G06K 9/0053; G06K 2009/00939; G06V 40/15
   See application file for complete search history.

(56) References Cited

U.S. PATENT DOCUMENTS

| | | | | |
|---|---|---|---|---|
| 2012/0136605 | A1* | 5/2012 | Addison | G16H 40/40 702/98 |
| 2012/0283581 | A1* | 11/2012 | Oide | A61B 5/0816 600/485 |
| 2014/0066785 | A1 | 3/2014 | Watson et al. | |
| 2014/0180043 | A1* | 6/2014 | Addison | A61B 5/14551 600/324 |
| 2016/0345907 | A1 | 12/2016 | Fung et al. | |
| 2017/0172510 | A1 | 6/2017 | Homyk et al. | |

OTHER PUBLICATIONS

Zhu, Qiang et al., "ECG Reconstruction Via PPG: A Pilot Study," cyclearXiv: 1904.10481v1, Apr. 2019, 4 pages.
Kavsaoglu, A. R., et al., "Feature Extraction for Biometric Recognition with Photoplethysmography Signals", Signal Processing and Communications Applications Conference (SIU), 2013 21st, Apr. 24-26, 2013, 4 pages.
Abe, E., et al., "Development of Drowsy Driving Accident Prediction by Heart Rate Variability Analysis", IEEE APSIPA, Dec. 2014, 4 pages.
Agro, D. et al., "PPG Embedded System for Blood Pressure Monitoring", Department of Energy, Information engineering, Mathematical models (DEIM), University of Palermo, STMicroelectronics, Sep. 18-19, 2014, 6 pages.
Allen, John, "Photoplethysmography and its application in clinical physiological measurement," IOP Publishing, Physiological Measurement, vol. 28, R1-R39, Topical Review, doi: 10.1088/0967-3334/28/3/R01, Mar. 2007, pp. R1-R39.
Arena, Paolo, et al., "Chaos control by using Motor Maps", Chaos Journal, vol. 12, No. 3, 2002, pp. 559-573.
Arena, P. et al., "A CNN-Based Chip for Robot Locomotion Control", IEEE Transactions on Circuits and Systems-I: Regular Papers, vol. 52, No. 9, Sep. 2005, pp. 1862-1871.
Arzi, M., "New algorithms for continuous analysis of long term ECG recordings using symplectic geometry and fuzzy pattern recognition", Computers in Cardiology, Sep. 25-28, 2005, pp. 739-742.
Banerjee, R., et al., "Estimation of ECG parameters using photoplethysmography", 13th IEEE International Conference on BioInformatics and BioEngineering, Nov. 10-13, 2013, pp. 1-5.
Battiato, S. et al., "ALZ: Adaptive Learning for Zooming Digital Images", Consumer Electronics, 2007, ICCE 2007, Digest of Technical Papers, International Conference, Jan. 10-14, 2007, 2 pages.
Bolanos, M., et al., "Comparison of heart rate variability signal features derived from electrocardiography and photoplethysmography in healthy individuals," IEEE Engineering in Medicine and Biology Society, EMBS '06, 28th Annual International Conference, New York City, Aug. 30-Sep. 3, 2006, pp. 4289-4294.

Dutt, et al., "Digital Processing of ECG and PPG Signals for Study of Arterial Parameters for Cardiovascular Risk Assessment", Communications and Signal Processing (ICCSP), Apr. 2-4, 2015, pp. 1506-1510.
Eftestol, T. et al., "A flexible pattern recognition system for analysis of ECG and related demographics and annotations", Proceedings of the 20th Annual International Conference of the IEEE Engineering in Medicine and Biology Society. vol. 20, No. 1, Biomedical Engineering, Nov. 1, 1998, pp. 135-138.
Elgendi, M., "On the Analysis of Fingertip Photoplethysomgram Signals", Current Cardiology Reviews, Journal List, Curr Cardiol Rev, V.8, Feb. 2012, pp. 14-25.
Ferdinando, H. et al., "Comparing features from ECG pattern and HRV analysis for emotion recognition system", Oct. 5-7, 2016 IEEE Conference on Computational Intelligence in Bioinformatics and Computational Biology, pp. 1-6.
Hagan, M.T., et al., "Training feedforward networks with the Marquardt algorithm," IEEE Transactions Neural Network, Nov. 1994; vol. 5, No. 6, pp. 989-993.
He, L. et al., "Recognition of ECG Patterns Using Artificial Neural Network", Sixth International Conference on Intelligent Systems Design and Applications, Oct. 16-18, 2006, pp. 477-481.
Jeyhani, V., et al., "Comparison of HRV parameters derived from photoplethysmography and electrocardiography signals," Engineering in Medicine and Biology Society (EMBC), 2015 37th Annual International Conference of the IEEE, Aug. 25-29, 2015, pp. 5952-5955.
Jin, F. et al., "The application of pattern recognition technology in the diagnosis and analysis on the heart disease Current status and future", May 23-25, 2012, 24th Chinese Control and Decision Conference (CCDC), pp. 1304-1307.
Liao, Jia-Ju et al., "An Effective Photoplethysomgraphy Signal Processing System Based on EEMD Method", Department of Electronics Engineering, National Chiao Tung University, Apr. 27-29, 2015, 4 pages.
Madhav, K., et al., "Estimation of respiration rate from ECG, BP and PPG signals using empirical mode decomposition," IEEE International Instrumentation and Measurement Technology Conference, May 10-12, 2011, 4 pages.
Mazzillo, M. et al., "Electro-Optical Performances of p-on-n and n-on-p Silicon Photomultipliers", IEEE Transactions on Electron Devices, vol. 59, No. 12, Dec. 2012, pp. 3419-3425.
Mazzillo, M. et al., "Silicon Photomultiplier Technology at STMicroelectronics", IEEE Transactions on Nuclear Science, vol. 56, No. 4, Aug. 2009, pp. 2434-2442.
Mazomenos, E. B., "A Time-Domain Morphology and Gradient based Igorithm for ECG Feature Extraction," IEEE International Conference on Industrial Technology (ICIT), Mar. 19-21, 2012, pp. 117-122.
Oreggia, D. et al., "Physiological parameters measurements in a cardiac cycle via a combo PPG-ECG system", Department of Energy, Information engineering and mathematical Models (DEIM)—University of Palermo, IMS R&D, STMicroelectronics, Oct. 14-16, 2015, 6 pages.
Page, A. et al., "Utilizing deep neural nets for an embedded ECG-based biometric authentication system", Oct. 22-24, 2015 IEEE Biomedical Circuits and Systems Conference (BioCAS), 4 pages.
Peng, F. et al., "Motion artifact removal from photoplethysmographic signals by comgining temporally constrained independent component analysis and adaptive filter", BioMedical Engineering OnLine Apr. 24, 2014, 14 pages.
Raghuram, M. et al., "Use of Complex EMD generated Noise Reference for Adaptive reduction of Motion Artifacts from PPG Signals", Dept, of E&I Engg., Kakatiya Institute of Technology & Science, Dept. of ECE, Talia Padmavathi College of Engineering, Kazipet, International Conference on Electrical, Electronics, and Optimization Techniques (ICEEOT)—2016, Mar. 3-5, 2016, pp. 1816-1820.
S.K. Deric Tang et al., "PPG Signal Reconstruction using a combination of Discrete Wavelet Transform and Empirical Mode Decom-

(56) References Cited

OTHER PUBLICATIONS position", Faculty of Engineering, Computing & Science, Swinburne University of Technology Sarawak Campus, Aug. 15-17, 2016, 4 pages.

Shin, Kun-Soo, et al., "An Algorithm for Pattern Recognition of Multichannel ECG Signals", Dept. of Electrical Engineering, Yonsei University, Seoul, Korea, Annual International Conferecne of the IEEE Engineering in Medicine and Biology Society, vol. 12, No. 2, Nov. 1-4, 1990, pp. 819-820.

Shorten, G.P. et al., "A time domain based classifier for ECG pattern recognition", 2011 33rd Annual International Conference of the IEEE Engineering in Medicine and Biology Society, Boston, Massachusetts, Aug. 30-Sep. 3, 2011, pp. 4980-4983.

Trahanias, P. et al., "Syntactic Pattern Recognition of the ECG", IEEE Transactions on Pattern Analysis and Machine Intelligence, vol. 12, No. 7, Jul. 1990, pp. 648-657.

Tuzcu, V. et al., "Dynamic time warping as a novel tool in pattern recognition of ECGchanges in heart rhythm disturbances", Oct. 12, 2005 IEEE International Conference on Systems, Man and Cybernetics, pp. 182-186.

Vicente, J. et al.: "Detection of Driver's Drowsiness by Means of HRV Analysis," IEEE Computing in Cardiology, Sep. 18-21, 2011; 38: pp. 89-92.

Vinciquerra, V., et al., "Progresses towards a Processing Pipeline in Photoplethysmogram (PPG) based on SiPMs", IEEE Proceedings of 23 European Conference on Circuit Theory and Design, Catania (Italy), Sep. 4-6, 2017, 5 pages.

Wu, Chih-Chin et al., "A Wireless Photoplethysmography Signal Processing System for Long-term Monitoring", IEEE International Conference on Consumer Electronics (ICCE), Mar. 14, 2016, pp. 480-483.

Yadhuraj S.R. et al., "GUI Creation for Removal of Motion Artifact in PPG Signals" 2016 3rd International Conference on Advanced Computing and Communication Systems (ICACCS—2016), Jan. 22-23, 2016, 5 pages.

Yeh, Ming-Feng et al., "ECG signal pattern recognition using grey relational analysis", IEEE International Conference on Networking, Sensing and Control, Mar. 21-23, 2004, pp. 725-730.

Fletcher, R. et al., "Function minimization by conjugate gradients," The Computing Journal, vol. 7, Issue 2, Jan. 1, 1964 pp. 149-154.

Kurylyak, Yuriy et al., "Smartphone-Based Photoplethysmogram Measurement," Department of Electronics, Computer and System Sciences, University of Calabria, Rende-CS, Italy, Jan. 2012, 30 pages.

Rundo, Francesco et al., "An Innovative Reaction-Diffusion Bio-Inspired Pipeline for Physiological Signals Analysis," ResearchGate, Conference Paper 2017, STMicroelectronics, Catania Italy, Oct. 2017, 2 pages.

Shin, Hangsik et al., "Feasibility study for the non-invasive blood pressure estimation based on ppg morphology normotensive subject study," Biomedical Engineering OnLine, XP055478171, Jan. 10, 2017, pp. 1-14.

Ali Hassan, M. K., et al., "Measuring Blood Pressure Using a Photoplethysmography Approach," 4th Kuala Lumpur International Conference on Biomedical Engineering, Jan. 2008, 5 pages.

Barbe, Kurt et al., "Analyzing the Windkessel Model as a Potential Candidate for Correcting Oscillometric Blood-Pressure Measurements," IEEE Transactions on Instrumentation and Measurement, vol. 61, No. 2, Feb. 2012, pp. 411-418.

Cattivelli, Federico S., et al., "Noninvasive Cuffless Estimation of Blood Pressure from Pulse Arrival Time and Heart Rate with Adaptive Calibration," Sixth International Workshop on Wearable and Implantable Body Sensor Networks, Jun. 3-5, 2009, 6 pages.

Datts, Shreyasi et al., "Blood Pressure Estimation from Photoplethysmogram using Latent Parameters," 2016 IEEE International Conference on Communications (ICC), May 22-27, 2016, 7 pages.

Fortino, Giancarlo et al., "PPG-based Methods for Non Invasive and Continuous Blood Pressure Measurement: an Overview and Development Issues in Body Sensor Networks," IEEE International Workshop on Medical Measurements and Applications, Apr. 30-May 1, 2010, 4 pages.

Gaurav, Aman et al., "Cuff-Less PPG based Continuous Blood Pressure Monitoring—A Smartphone based Approach," 38th Annual International Conference of the IEEE Engineering in Medicine and Biology Society (EMBC), Aug. 16-20, 2016, 4 pages.

Goldberger, Ary L., et al., "PhysioBank, PhysioToolkit, and PhysioNet Components of a New Research for Complex Physiologic Signals," American Heart Association, Inc., Circulation, Jun. 13, 2000; 101(23): E215-20, 7 pages.

Gu, W. B., et al., "A Novel Parameter from PPG Dicrotic Notch for Estimation of Systolic Blood Pressure Using Pulse Transit Time," Proceedings of the 5th International Workshop on Wearable and Implantable Body Sensor Networks, in conjunction with the 5th International Summer School and Symposium on Medical Devices and Biosensors, Chinese University of Hong Kong, HKSAR, China, Jun. 1-3, 2008, 3 pages.

Huang, Yo-Ping et al., "Early Detection of Driver Drowsiness by WPT and FLFNN Models," IEEE International Conference on Systems, Man, and Cybernetics (SMC), Budapest, Oct. 9-12, 2016, pp. 000463-000468.

Hwang, Taeho et al., "Driver Drowsiness Detection Using the In-Ear EEG," 38th Annual International Conference of the IEEE Engineering in Medicine and Biology Society (EMBC), Orlando, FL., Aug. 16-20, 2016, pp. 4646-4649.

Kao, Young-Hua et al., "A PPG Sensor for Continuous Cuffless Blood Pressure Monitoring with Self-Adaptive Signal Processing," Proceedings of the International Conference on Applied System Innovation (ICASI), IEEE-ICASI, 2017—Meen, Prior & Lam (Eds), May 13-17, 2017, 4 pages.

Kim, Jung Yi et al., "Comparative study on artificial neural network with multiple regressions for continuous estimation of blood pressure," Proceedings of the IEEE, Engineering in Medicine and Biology 27th Annual Conference, Shanghai, China, Sep. 1-4, 2005, 4 pages.

Kurylyak, Yuriy et al., "A Neural Network-based Method for Continuous Blood Pressure Estimation from a PPG Signal," IEEE International Instrumentation and Measurement Technology Conference (12MTC), May 6-9, 2013, pp. 280-283.

Lamonaca, F., et al., "Reliable Pulse Rate Evaluation by Smartphone," IEEE International Symposium on Medical Measurements and Applications Proceedings, May 18-19, 2012, 4 pages.

Lawoyin, Samual, "Novel technologies for the detection and mitigation of drowsy driving," VCU Virginia Commonwealth University, VCU Scholars Compass, Thesis and Dissertations, http://scholarscompass.vcu.edu/etd/3639, Dec. 2014, 320 pages.

Lee, Jaewon et al., "Correlation Analysis between Electrocardiography (ECG) and Photoplethysmogram (PPG) Data for Driver's Drowsiness Detection Using Noise Replacement Method," Procedia Computer Science, vol. 116, Oct. 13-14, 2017, pp. 421-426, ISSN 1877-0509.

Li, Gang et al., "Detection of Driver Drowsiness Using Wavelet Analysis of Heart Rate Variability and a Support Vector Machine Classifier," Sensors (Basel, Switzerland), Dec. 2013(12), www.mdpi. com/journal/sensors, pp. 16494-16511.

Liu, Mengyang et al., "Cuffless Blood Pressure Estimation Based on Photoplethysmography Signal and its Second Derivative," International Journal of Computer Theory and Engineering, vol. 9, No. 3, XP055478166, Jun. 2017, pp. 202-206.

Lu, Guohua et al., "A comparison of photoplethysmography and ECG recording to analyse heart rate variability in healthy subjects," Journal of Medical Engineering & Technology, vol. 33, ISSN: 0309-1902, Dec. 15, 2009, pp. 634-641.

McCombie, Devin B., et al., "Adaptive blood pressure estimation from wearable PPG sensors using peripheral artery pulse wave velocity measurements and multi-channel blind identification of local arterial dynamics," Proceedings of the 28th IEEE, EMBS Annual International Conference, New York City, USA, Aug. 30-Sep. 3, 2006, 4 pages.

(56) References Cited

OTHER PUBLICATIONS

Meigas, Kalju et al., "Continuous Blood Pressure Monitoring Using Pulse Wave Delay," IEEE Proceedings of the 23rd Annual EMBS International Conference, Oct. 25-28, 2001, Istanbul, Turkey, pp. 3171-3174.

Rundo, F., et al., "An Advanced Bio-Inspired PhotoPlethysmoGraphy (PPG) and ECG Pattern Recognition System for Medical Assessment," Sensors, vol. 18, 405, Jan. 2018, 22 pages.

Saravanamoorthi, A., et al., "Prediction of Drowsy Fault Using Bio Signals Joint Stachostic FSD (BJSFSD) Algorithm," European Journal of Applied Sciences 8 (4): 193-199, Aug. 2014, 7 pages.

Sari, Nila Novita et al., "A Two-Stage Intelligent Model to Extract Features from PPG for Drowsiness Detection," IEEE International Conference on System Science and Engineering (ICSSE), Jul. 7-9, 2016, pp. 1-2.

Selvaraj, N.,, et al., "Assessment of heart rate variability derived from finger-tip photoplethysmography as compared to electrocardiography," Journal of Medical Engineering & Technology 2008, pp. 479484.

Shin, Heung-Sub, et al., "Real Time Car Driver's Condition Monitoring System," Sensors, IEEE, Nov. 1, 2010, pp. 951-954.

Soltane, Mohamed et al., "Artificial neural networks (ANN) Approach to PPG Signal Classification," International Journal of Computing & Information Sciences, Apr. 2004, vol. 2(1), pp. 58-65.

Takagi, Tomohiro et al., "Fuzzy Identification of Systems and its Applications to Modeling and Control," IEEE Transactions on Systems, Man, and Cybernetics, vol. SMC-15, No. 1, Jan. / Feb. 1985, pp. 116-132.

Teng, X. F., et al., "Continuous and Noninvasive Estimation of Arterial Blood Pressure Using a Photoplethysmographic Approach," Proceedings of the 25th Annual International Conference of the IEEE EMBS, Cancun, Mexico, Sep. 17-21, 2003, 4 pages.

Yan, Y. S., et al., "Noninvasive Estimation of Blood Pressure Using Photoplethysmographic Signals in the Period Domain," IEEE Engineering in Medicine and Biology 27th Annual Conference, Jan. 17-18, 2006, pp. 3583-3584.

Yoon, Youngzoon et al., "Nonconstrained Blood Pressure Measurement by Photoplethysmography," Journal of the Optical Society of Korea, vol. 10, No. 2, Jun. 2006, pp. 91-95.

\* cited by examiner

PPG_REF

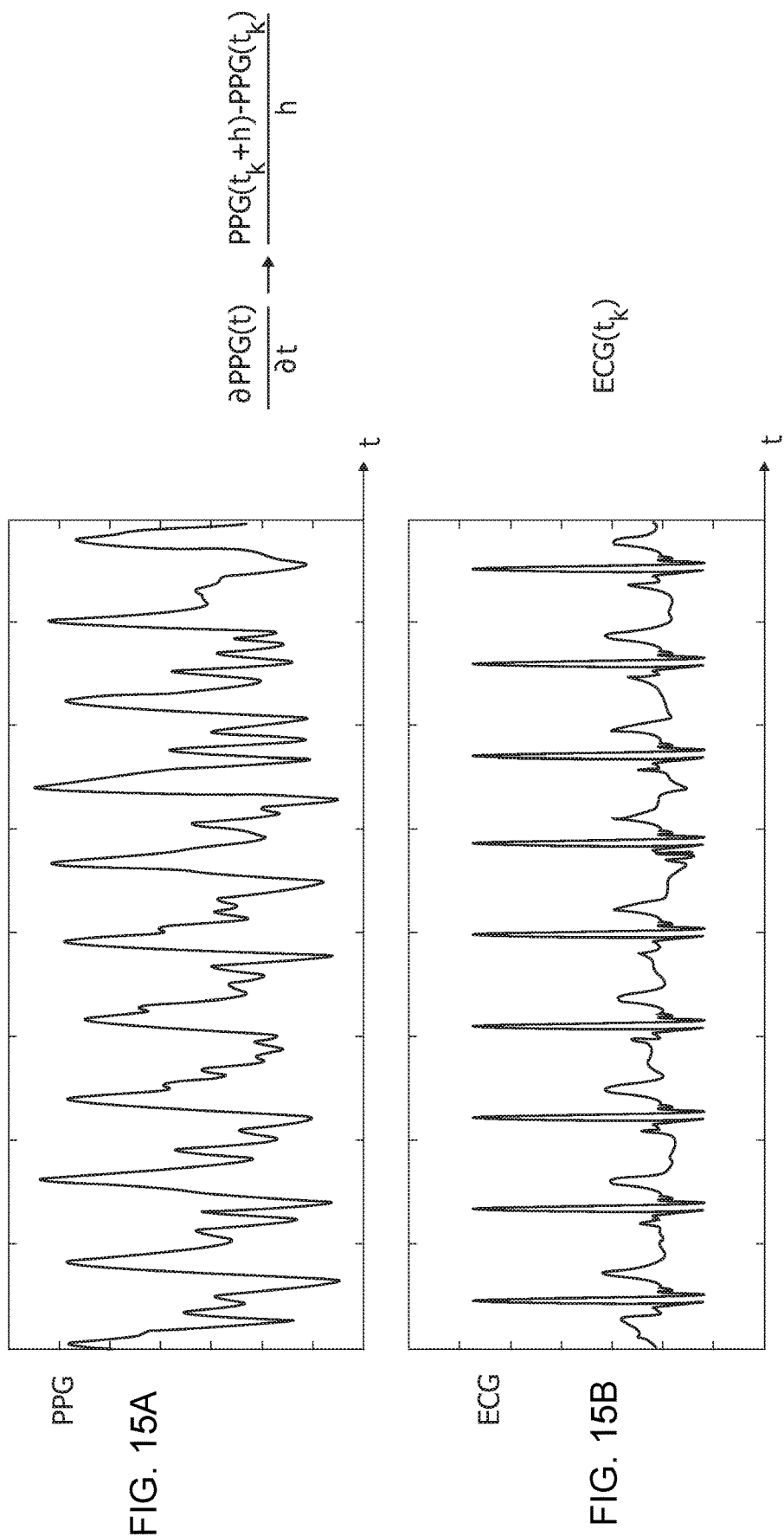

PROCESSING OF ELECTROPHYSIOLOGICAL SIGNALS

CROSS-REFERENCE TO RELATED APPLICATIONS

This application claims priority to Italian Patent Application No. 102017000081018, filed on Jul. 18, 2017, which application is hereby incorporated herein by reference.

TECHNICAL FIELD

This disclosure relates generally to a processing system, and, in particular embodiments, to processing of electrophysiological signals.

BACKGROUND

Electrocardiography (ECG) is the process of recording the electrical activity of the heart over a period of time using electrodes placed on the skin. These electrodes detect the tiny electrical changes on the skin that arise from electrophysiological patterns of de-polarization and re-polarization which occur during each heartbeat of the heart muscle. Electrocardiography is a cardiology test very commonly performed.

A typical ECG waveform includes two intervals:

a PR interval that includes a P waveform and a so-called PR segment, and a QT interval, which includes Q, R, S waveforms (QRS complex), a ST segment and a T waveform.

Detecting and processing ECG signals is the subject-matter of extensive literature, e.g., such as:

G. P. Shorten; M. J. Burke: "A time domain based classifier for ECG pattern recognition," 2011 Annual International Conference of the IEEE Engineering in Medicine and Biology Society, pp. 4980-4983;

Lin He; Wensheng Hou; Xiaolin Zhen; Chenglin Peng: "Recognition of ECG Patterns Using Artificial Neural Network," Sixth International Conference on Intelligent Systems Design and Applications, 2006, pp. 477-481;

P. Trahanias; E. Skordalakis: "Syntactic pattern recognition of the ECG," IEEE Transactions on Pattern Analysis and Machine Intelligence, 1990, pp. 648-657;

Hany Ferdinando; Tapio Seppinen; Esko Alasaarela: "Comparing features from ECG pattern and HRV analysis for emotion recognition system," 2016 IEEE Conference on Computational Intelligence in Bioinformatics and Computational Biology, pp. 1-6;

M. Arzi: "New algorithms for continuous analysis of long term ECG recordings using symplectic geometry and fuzzy pattern recognition," Computers in Cardiology, 2005, pp. 739-742;

V. Tuzcu; S. Nas: "Dynamic time warping as a novel tool in pattern recognition of ECGchanges in heart rhythm disturbances," 2005 IEEE International Conference on Systems, Man and Cybernetics, pp. 182-186;

Ming-Feng Yeh; Ying-Jen Chen; Kuang-Chiung Chang: "ECG signal pattern recognition using grey relational analysis," IEEE International Conference on Networking, Sensing and Control, 2004, pp. 725-730;

Kun-Soo Shin; Seon-Cheol Hwang; Byung-Chae Lee; Nyoung-Ho Lee: "An algorithm for pattern recognition of multichannel ECG signals," Proceedings of 20th Annual International Conference of the Engineering in Medicine and Biology Society, 1990, pp. 819-820;

T. Eftestol; S. O. Aase; J. H. Husoy: "A flexible pattern recognition system for analysis of ECG and related demographics and annotations," Proceedings of the 20th Annual International Conference of the IEEE Engineering in Medicine and Biology Society. Vol. 20 Biomedical Engineering, 1998, pp. 135-138;

Adam Page; Amey Kulkarni; Tinoosh Mohsenin: "Utilizing deep neural nets for an embedded ECG-based biometric authentication system," 2015 IEEE Biomedical Circuits and Systems Conference (BioCAS), pp. 1-4; and Feiming Jin; Jihong Liu; Weigang Hou: "The application of pattern recognition technology in the diagnosis and analysis on the heart disease: Current status and future," 2012 24th Chinese Control and Decision Conference (CCDC), pp. 1304-1307.

Various approaches in processing ECG signals may include using:

conventional digital filters (FIR/IIR);

conventional DTW (Dynamic Time Warping);

heuristic algorithms;

neural networks and fuzzy systems; and deep learning methods.

These approaches may result in an ECG signal processing pipeline having various limitations such as, for example:

high complexity of the system, which may result, e.g., in a long computational time, which may not be compatible with time constraints applicable to medical devices;

a modest sensitivity/specificity ratio with high computational costs;

arrangements based on neural networks or fuzzy systems involve training sessions (e.g., in connection with over-fitting issues, neural network topology, training algorithms, etc.) or self-tuning of adaptive parameters;

certain arrangements are not easy to implement (irrespective of whether software-based or hardware-based); and certain correlations may exist with other physiological signals of the patient.

PhotoPlethysmoGraphy (PPG) is a simple and low-cost optical technique that can be used to detect blood volume changes in the microvascular bed of human tissue. PhotoPlethysmoGraphy is often used in a non-invasive manner to make measurements at the skin surface.

A PPG waveform comprises a pulsatile ('AC') physiological waveform which can be attributed to cardiac-synchronous changes in the blood volume with each heartbeat, superimposed on a slowly varying ('DC') baseline with various lower frequency components which can be attributed to respiration, thermoregulation, the nature of skin tissues, and so on.

For each cardiac cycle, the heart pumps blood to the periphery. This pressure pulse is somewhat damped by the time it reaches the skin, but is enough to distend the arteries and arterioles in the subcutaneous tissue. If a light reflex/transmit detector device is attached over the skin, a pressure pulse can also be seen from the venous plexus, as a small secondary peak.

The change in volume caused by the pressure pulse can be detected by illuminating the skin with light from a light-emitting diode (LED) and then by measuring the amount of light either transmitted or reflected to a photodiode. Each cardiac cycle appears as a peak.

Blood flow to the skin can be modulated by multiple other physiological systems and PPG can also be used to monitor breathing, hypovolemia, and circulatory conditions as well as for subjective analysis.

Additionally, the shape of the PPG waveform differs from subject to subject, and varies with the location and manner in which the pulse oximeter is attached.

Use of PPG may be envisaged also in areas other than the medical field. For instance, PPG has been considered for use in the automotive field, e.g., in order to gain useful information on the behavior and/or the reaction of drivers and passengers in various situations which may occur in a motor vehicle.

SUMMARY

One or more embodiments may be applied to processing electrophysiological signals such as, e.g., ElectroCardioGraphy (ECG) and/or PhotoPlethysmoGraphy (PPG) signals.

One or more embodiments relate to a method of processing electrophysiological signals.

One or more embodiments may relate to a corresponding system.

One or more embodiments may include a computer program product loadable in the memory of at least one processing circuit (e.g., a computer) and including software code portions for executing the steps of the method when the product is run on at least one processing circuit. As used herein, reference to such a computer program product is understood as being equivalent to reference to a computer-readable medium containing instructions for controlling the processing system in order to coordinate implementation of the method according to one or more embodiments. Reference to "at least one computer" is intended to highlight the possibility for one or more embodiments to be implemented in modular and/or distributed form.

One or more embodiments may involve a pipeline configured for processing PhotoPlethysmoGraphy (PPG) signals based on the use of detectors such as e.g., of Silicon PhotoMultiplier (SiPM) detectors. Such probe sensors may provide advantages in terms of single-photon sensitivity and high internal gain for relatively low reverse bias.

One or more embodiments may adopt (possibly in connection with SiPM detectors) a processing pipeline adapted to correct signal distortion.

One or more embodiments may adopt a processing pipeline including a PPG raw signal filter, in turn including an, e.g., FIR pass-band scheme (e.g., low-pass plus high-pass), a PPG pattern recognition system as well as a system for detecting and extract medical indicators.

One or more embodiments may adopt nonlinear dynamics with specific features different from a PPG signal. For instance, a non-linear signal pattern can be fed to a processing pipeline, with analysis of the resulting output adapted to reveal (with good level of reliability) that processing occurred according to embodiments.

One or more embodiments thus facilitate obtaining information (data, physical quantities) from the living human or animal body, e.g., in support of the diagnostic activity of a human in medical and veterinary activities or for other possible uses. Obtaining information on the behavior and/or the reaction of drivers and passengers in the automotive field is exemplary of one such possible use.

One or more embodiments may facilitate ECG signal processing (i.e., ECG waveform pattern recognition) applied in a PPG/ECG system including, for example:

ECG/PPG sensors (e.g., Silicon PhotoMultipliers—SiPM for PPG sensing);

a digital filter block for preliminary filtering of ECG/PPG raw signals;

a "bio-inspired" PPG Pattern Recognition System—BI-P2RS; and a "bio-inspired" ECG Pattern Recognition System—BI-ECG-PR.

One or more embodiments may involve an ECG signal processing pipeline that facilitates efficient segmentation of compliant ECG waveforms in a combined PPG/ECG system, which in turn facilitates robust HRV (Heart Rate Variability) estimation.

One or more embodiments may offer one or more of the following advantages: high-speed computation facilitated by pattern recognition mechanisms based on 1-D signal data analysis; low complexity of data analysis; training algorithms or self-tuning of system parameters can be avoided; simple implementation for ECG/PPG signal acquired (e.g., based on a STM32 platform as currently available with companies of the STMicroelectronics group); high sensitivity/specificity ratio (e.g., 98%/98%) versus low complexity design; high robustness and accuracy of ECG recognition due to uncorrelated methods of ECG pattern analysis.

One or more embodiments may use a specific ECG pattern/signal fed into a processing pipeline in order to track an output correlated with a specific design method. This facilitates ECG pattern recognition involving mathematical correlation and medical assessment of a segmented ECG waveform (BCG/dPPG/dt/ECG).

BRIEF DESCRIPTION OF THE DRAWINGS

One or more embodiments will now be described, by way of example only with reference to the annexed figures, wherein:

FIGS. 15A and 15B, respectively, are exemplary of the possible time behavior of certain signals in embodiments.

DETAILED DESCRIPTION OF ILLUSTRATIVE EMBODIMENTS

Figure 1:
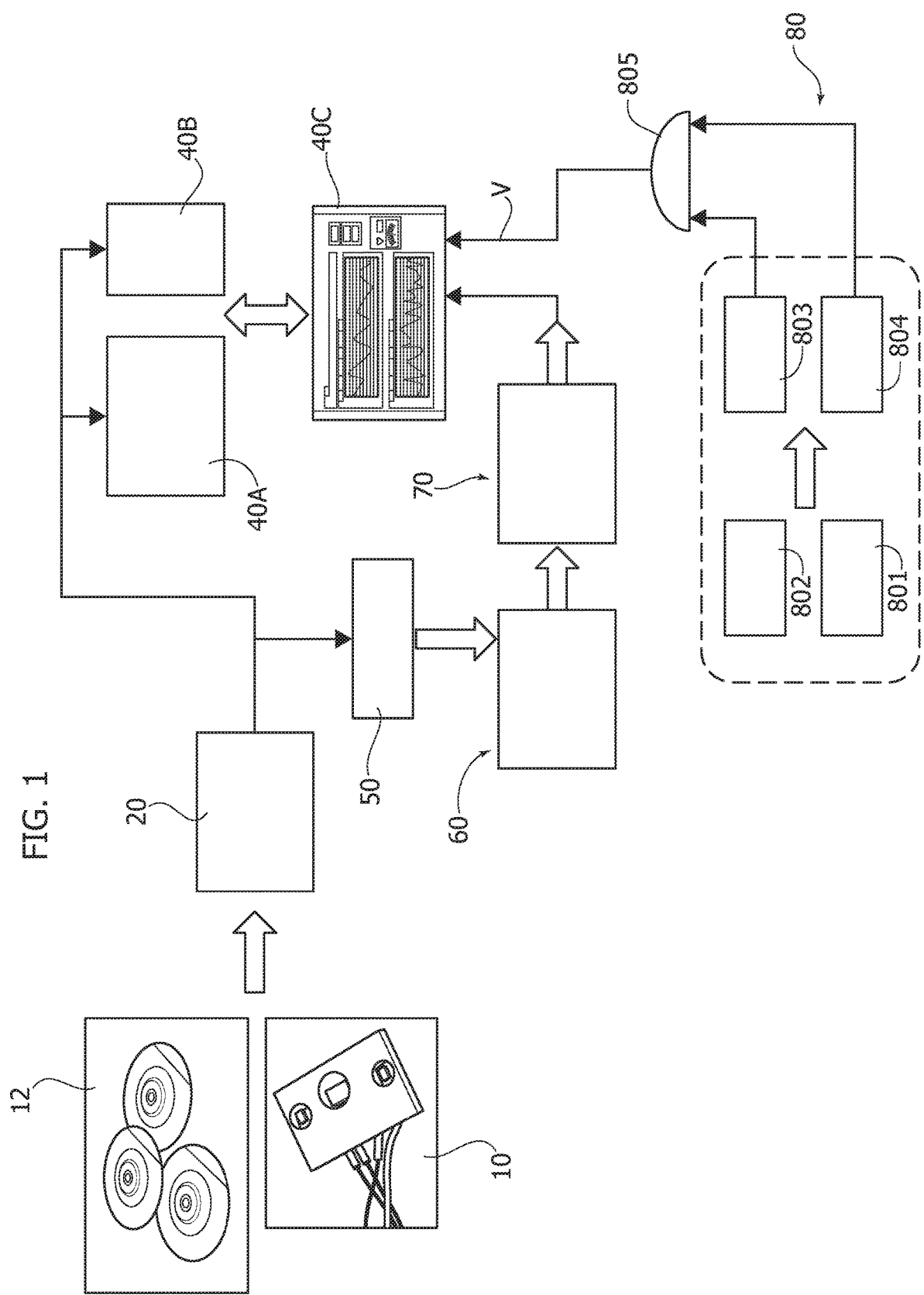
FIG. 1 is block diagram exemplary of a possible general architecture of embodiments.

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

The detailed exemplary description provided herein will refer to a pattern recognition arrangement adapted for performing processing of "raw" PhotoPlethysmoGraphy (briefly "PPG") signals acquired via a multichannel ECG+PPG combination ("combo") portable system. A corresponding system as exemplified herein will thus include a set of probes, an analog front-end, and a main PPG/ECG, e.g., embedded subsystem.

It will be otherwise appreciated that PPG signal processing apparatus as exemplified herein may be used independently of any ECG processing arrangement, and, more generally, in areas other than the medical field. For instance, a PPG signal processing arrangement as exemplified herein can be used in the automotive field in order to gain useful information on the behavior and/or the reaction of drivers and passengers in various situations which may occur in a motor vehicle.

PPG probes as exemplified herein may include a 940 nm LED and a silicon photomultiplier (SiPM) detector providing good responsivity and high gain. The ADS1194 biopotential measurements sampling family available from Texas Instruments was found to offer good scalability and up to four simultaneous sampling channels (16-bit resolution, IkSPS sampling rate) in possible use with such probes.

In possible applications in the medical field, one or more embodiments can contemplate real-time monitoring of cardiovascular parameters with simultaneous acquisition of two PPG waveforms at different body locations and one ECG lead. This was found to provide adequate quality of the acquired signals, making it possible, e.g., to extract an Augmentation Index from a single measurement on the wrist (rather than from a pressure wave) to estimate the arterial stiffness.

In one or more embodiments as exemplified herein, a collected PPG raw signal is preliminary filtered through a conventional IIR filter including low-pass and high-pass filters and then processed via self-adaptive pipeline using a nonlinear system. It was noted that such a PPG signal may be affected by noise and signal-distortion due to breath activity, motion artifacts, and micro-vibrations and may benefit from further processing. This may involve, e.g., preliminary first and second derivative computation performed to detect relative maximum and minimum values, possibly followed by normalization in the range [0, 1], and a basic segmentation of the collected PPG time series, assuming that a compliant PPG waveforms can be found between two subsequent valleys (minimum values).

In one or more embodiments, possible issues related to corrupted PPG signals may be addressed by resorting to a self-adaptive nonlinear oscillator configured to generate a compliant PPG waveform according to a mathematical model of the PPG signal.

For instance, for each collected PPG segmented waveform, a reference PPG signal can be rescaled over time using a "nearest" algorithm to get time-comparable waveforms (reference and collected). A sample cross-correlation analysis between rescaled-normalized PPG waveforms can be finally performed in a pattern recognition pipeline, with high-correlation PPG waveforms accepted and used to build a robust, clean PPG time series, while low-correlation PPG waveforms are discarded.

The results collected by using such a recognition pipeline exhibit robustness and efficiency in terms of sensibility/specificity ratio of the proposed approach.

With reference to possible applications in the medical field, one or more embodiments can provide a platform that facilitates the medical assessment of PPG/ECG signals by a human practitioner, with ECG signals adapted to be "validated" on the basis of PPG signals.

PPG/ECG coupled signals found to be compliant to the medical standard for these physiological waveforms facilitate obtaining robust and proper medical measures, by dealing with various factors such as, e.g., electronic noise, body movements, motion artifacts, body tissue issues, and breath and heart activity during the measuring session, which may corrupt both PPG and ECG signals.

One or more embodiments can provide a "bio-inspired" pipeline for real-time simultaneous adaptive pattern processing of PPG and ECG signal, with preliminary pre-filtering of the PPG/ECG signals is performed by using IIR Low/High pass filters.

In one or more embodiments, a mathematical analysis of the PPG signal can be performed in order to detect certain relative extremes, i.e., systolic peak (maximum), notch, diastolic peak, and minimum of the PPG waveform, with identification of each PPG waveform acquired facilitated by adaptive segmentation of the collected pre-filtered PPG time series.

One or more embodiments may adopt a Reaction-Diffusion mathematical model to provide a PPG compliant reference signal for robust pattern recognition of the collected pre-filtered signal. Such a Reaction-Diffusion model can associate the diastolic phase of the heart to a "reaction" physical model while the "systolic phase" can be modelled as having "Diffusion" physical proprieties.

One or more embodiments may rely on an observable cross-correlation between an ECG signal and the first-derivative of an associated, processed PPG waveform, for a same patient. The compliant first-derivative PPG waveform can thus be used for analyzing a related ECG waveform obtained by automatic segmentation of pre-filtered ECG in the same PPG time onset. Both first-derivative PPG and ECG waveforms can be normalized over the interval [0, 1].

A pipeline according to one or more embodiments can perform sample cross-correlation analysis of these signals by using time rescaling by relying on the observed high cross-correlation of a compliant ECG waveform with respect to a corresponding first-derivative PPG waveform. Collected compliant ECG waveforms can be used as a reference pattern for subsequent ECG analysis.

As noted, PhotoPlethysmoGraphy (PPG) is becoming increasingly popular a non-invasive technique adapted to provide information on the cardiovascular system, in particular, the heart pulse rate. A PPG sensor consists of a Light Emitting Diode (LED) used as an optical light source and a photodetector. A PPG sensor monitors changes in the light intensity via backscattering from or transmission through the body tissue, thus detecting blood flow volume changes in arterial vessels which cause a change in light absorption, and, therefore, in the detected light intensity. A typical PPG waveform includes a direct current (DC) component and alternating current (AC) components. The DC component depends on the average blood volume of the arterial and venous blood. The (relatively smaller) AC component is indicative of changes in the blood volume occurring between the systolic and diastolic phases of the cardiac cycle and is superimposed onto the DC component with a fundamental frequency depending on the heart beat rate (see, e.g., J. Allen: "Photoplethysmograpy and its application in clinical physiologic measurement," Physiological Measurement, vol. 28, no. no. 3, pp. R1-R39, April 2007).

Accurate monitoring of dynamic changes of physiological data through a non-invasive integrated system, including hemodynamic parameters (e.g., heart rate, blood pressure, tissue perfusion) and heart electrical activity can play an important role in a variety of applications (e.g., healthcare, fitness and cardiovascular disease).

Increased interest thus exists for integrated, low-power consumption, wireless and portable PhotoPlethysmoGraphy-ElectroCardioGraphy (briefly PPG-ECG) combination ("combo") systems facilitating assessing these physiological parameters and their ubiquitous monitoring over time (see e.g., D. Oreggia, et al.: "Physiological parameters measurements in a cardiac cycle via a combo PPG-ECG system," in AEIT International Annual Conf, 2015).

It was observed (see e.g., D. Agrò, et al.: "PPG embedded system for blood pressure monitoring," in AEIT Annual Conference—From Research to Industry: The Need for a More Effective Technology Transfer (AEIT), Trieste, 2014), that Silicon PhotoMultipliers (SiPM's) can provide advantages in PPG systems in terms of higher AC-to-DC ratio in PPG pulse waveform, high repeatability and immunity to motion artifacts and ambient interferences.

One or more embodiments as discussed herein provide improvements in PPG techniques by using SiPMs (as available with companies of the ST group) as optical probe sensors, adapted to be used in conjunction with hardware and software components in providing a signal processing pipeline.

A block diagram exemplary of a possible general architecture of embodiments is shown in FIG. 1.

The block diagram of FIG. 1 includes one or more PPG probes 10 and one or more ECG probes 12.

For instance, the platform as exemplified herein can include a coupled LED-Silicon photomultiplier (SiPM) detector, e.g., silicon SiPM's with a total area of 4.0×4.5 mm$^2$ and 4871 square microcells with 60 micron (1 micron=10$^{-6}$ m) pitch along with OSRAM LT M673 LEDs in SMD package emitting at two selected wavelengths.

The ECG probes 12 can be of conventional type. For instance, a transmission setup for PPG detection can be used along with classical electrical detectors (at least three as per Einthoven's triangle) for acquiring ECG signal simultaneously.

It will be once again recalled that the following discussion within the framework of a combined PPG/ECG sensing arrangement is merely exemplary and not limitative of the embodiments. PPG signal processing apparatus as described in the following can be used independently of any ECG processing arrangement, and, more generally, in areas other than the medical field, e.g., in the automotive field. For that reason, emphasis will be placed in the following discussion primarily on processing of PPG signals.

Figure 2:
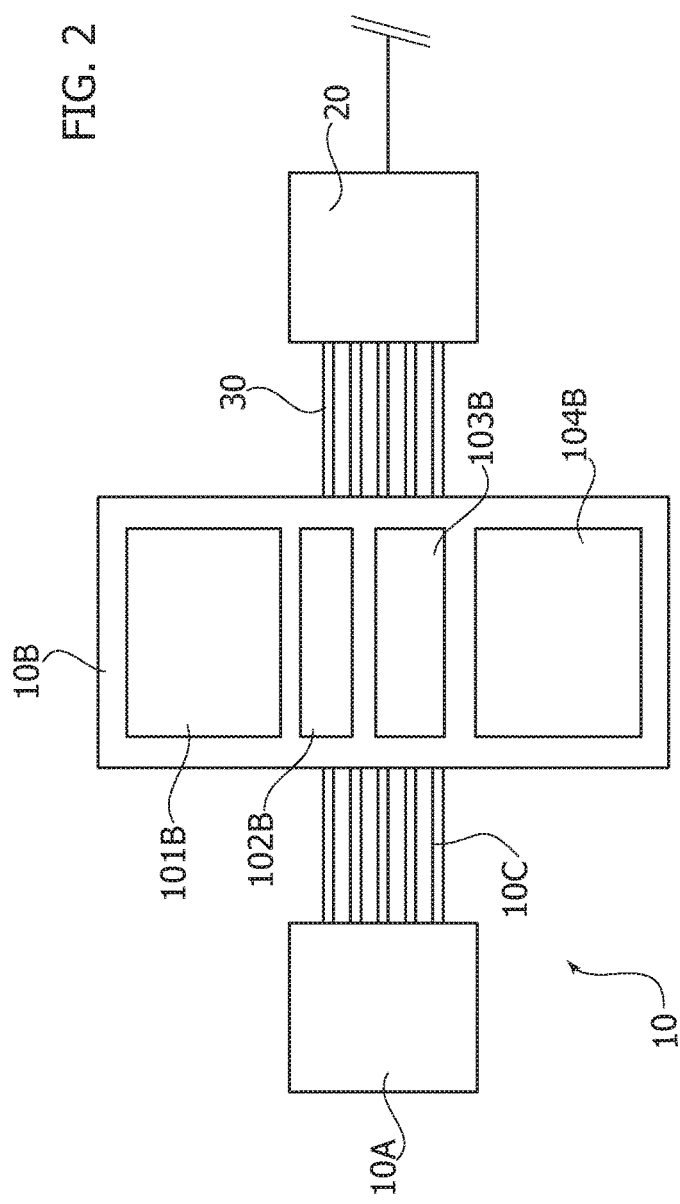
FIG. 2 is a block diagram exemplary of a possible logical configuration of certain parts of embodiments.

As shown in FIG. 2, in one or more embodiments, the probe circuitry block indicated as a whole as 10 in FIG. 1 can include a PPG probe section 10A and an printed circuit board (PCB) 10B configured for interfacing the probe sections 10A with an acquisition and processing circuit 20. In the exemplary arrangement shown, the PPG probe section 10A can be coupled to the interface PCB 10B via, e.g., USB cables 10C with the interface PCB 10B in turn coupled with the circuit 20 via, e.g., SubMiniature version A (SMA) cables 30. Other arrangements known in the art for these purposes may be adopted for the connections 10C, 30.

In one or more embodiments, the probe section 10A can include SiPMs having associated, in a manner known per se, various ancillary components such as bandpass filters, LEDs, sensing resistors, and bias capacitances.

In one or more embodiments, the interface PCB 10B can include a power management section 101B (e.g., a portable battery, a voltage regulator, SiPM bias circuitry), a LED driver section 102B, and output signal conditioning circuits 103B, as well as connectors (e.g., USB and SMA) 104B.

In one or more embodiments, the PPG probe section 10A can be based on the use of large area n-on-p SiPMs fabricated at STMicroelectronics (see, e.g., M. Mazzillo, et al.: "Silicon Photomultiplier technology at STMicroelectronics," IEEE Trans. Nucl. Sci, vol. 56, no. 4, pp. 2434-2442, 2009). As noted, these SiPMs have a total area of 4.0×4.5 mm$^2$ and 4871 square microcells with 60 micron (1 micron=10$^{-6}$ m) pitch. These devices have a geometrical fill factor of 67.4% and are packaged in a surface mount housing (SMD) with 5.1×5.1 mm$^2$ total area (see e.g., M. Mazzillo, et al., cited above or M. Mazzillo, et al.: "Electro-optical performances of p-on-n and n-on-p silicon photo-multipliers," IEEE Trans. Electron Devices, vol. 59, no. 12, pp. 3419-3425, 2012).

A Pixelteq dichroic bandpass filter with a pass band centered at 542 nm with a Full Width at Half Maximum (FWHM) of 70 nm and an optical transmission higher than 90% in the pass band range can be glued on the SMD package by using a Loctite® 352™ adhesive. With the dichroic filter at 3V-OV the SiPM has a maximum detection efficiency of about 29.4% at 565 nm and a PDE of about 27.4% at 540 nm (central wavelength in the filter pass band). It was noted that the dichroic filter can reduce in excess of 60% the absorption of environmental light in the linear operation range of the detector operating in Geiger mode above its breakdown voltage (~27V). OSRAM LT M673 LEDs in SMD package emitting at 529 nm and based on InGaN technology have been used as optical light sources in exemplary embodiments. These LEDs have an area of 2.3×1.5 mm$^2$, viewing angle of 120°, spectral bandwidth of 33 nm and typical power emission of a few milliwatts in the standard operation range.

In one or more embodiments, the printed circuit board (PCB) 10B can be designed and used to interface the PPG probe(s) and, e.g., an NI (National Instrument) acquisition instrumentation 20 during the measurement of the PPG signals.

In one or more embodiments, the PCB 10B can host a 4 V portable battery and a power management circuit (in section 101B), a conditioning circuit (section 103B) for output SiPMs signals, eight mini B-USB connectors for PPG probes, and eight SMA output connectors (section 104B). The voltage regulator (section 101B) can be set at e.g., 3.3 V to provide a power supply for the optical parametric amplifier (OPA) and the LED driver circuits (section 102B).

In one or more embodiments, the PCB 10B can host a step-up DC-DC converter to generate a 30 V output and provide a bias to the SiPMs. Trimmers on the PCB allow adjustment of the LEDs brightness in the PPG probe(s).

The continuous (DC) component in the SiPM output signals can be at least partially eliminated by using a differential signal acquisition configuration in the signal conditioning circuit, with a gain set to, e.g., 30 by using a (single) external resistor. The subtraction of the continuous (DC) part is adjustable by using a trimmer to facilitate adequate output signal acquisition in each (analog-to-digital—ADC) channel.

In one or more or more embodiments, the acquisition instrumentation circuit 20 can be coupled (in an otherwise conventional manner) to a signal presentation set including, e.g., a graphical user interface (GUI) 40A, possibly in conjunction with a data logger 40B, and a display unit (e.g., a screen and/or a printer) 40C so that the (here ECG/PPG) signals acquired by using the acquisition instrumentation 20 can be presented to an operator, e.g., a medical practitioner, to enable him or her to follow the acquisition process, with these "raw" signals possibly logged at 40B.

In one or more embodiments, these raw data can also be collected at 50 in view of processing in a processing circuit 60. Such a circuit as exemplified herein may include a hardware/software platform based on, e.g., a personal computer (e.g., with Intel core i5 3.4 GHz plus MATLAB) configured to acquire and process PPG (and EGC) signals, as discussed in the following.

In one or more or more embodiments the circuit 60 may be configured to implement a PPG pattern recognition system (e.g., pipeline) 70 and a ECG pattern recognition/validation system (e.g., pipeline) 80.

The results produced by the circuit 60 (systems 70 and 80) can possibly be presented on the display unit 40C to an operator, e.g., a medical practitioner, with the capability of supporting his activity, e.g., for diagnostic purposes.

As repeatedly noted in the foregoing, PPG processing apparatus as discussed herein lends itself to be used in areas other than the medical field, e.g., in the automotive field in order to gain useful information on the behavior and/or the reaction of drivers and passengers in various situations which may occur in a motor vehicle.

In comparison with the combined PPG/ECG acquisition/processing system exemplified herein, such "automotive" PPG apparatus will not include those blocks exemplified herein (e.g., the probes 12, the processing system 80) that are related to the ECG signals (that is the medical use). Also, the presentation set 40A, 40B, and 40C will be correspondingly adapted to the different use and purposes of use.

Figure 3:
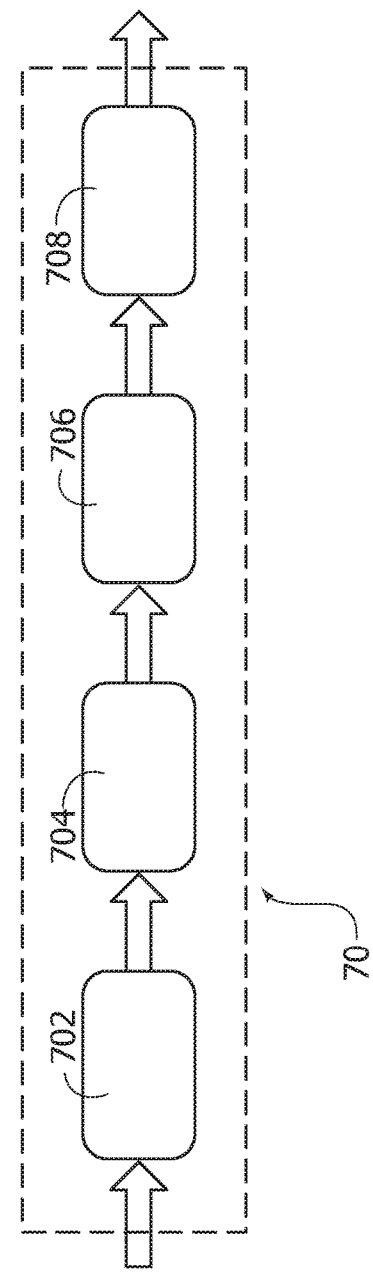
FIG. 3 is a block diagram of a signal processing pipeline in embodiments.

In one or more embodiments, the PPG signal processing system or pipeline 70 receiving the PPG raw signals at 50 may include the blocks exemplified in FIG. 3. A filtering block 702 (e.g., a FIR/IIR low-pass section and a FIR/IIR high-pass section) receives the raw PPG signal. A pattern recognition (PR) block 704 is coupled to the output of the block 702. A PPG medical indicator detection block 706 is coupled to the output of the block 704. A block 708 is coupled to the output of the block 706 and adapted to perform other functions related to parameters such as e.g., pulse wave velocity (PWV), pulse transit time (PTT), cardiovascular assessment stage (A1), artery stiffness, blood pressure measurement/monitoring, beats per minute (BPM) and so on.

One or more embodiments may be based on the recognition that a HW/SW platform used for sensing PPG signals, possibly in conjunction with ECG signal, as is the case of the "combo" system exemplified herein, may be sensitive to (involuntary) movements of the patient, electronic noise (e.g., power supply noise) and light scattering. Also, the sampled PPG signal may be affected by artifacts that can result in distortion of final acquired PPG wave in some sampling intervals.

In one or more embodiments, noise and signal distortion (which may residue even after careful filtering of the raw signal, e.g., at 702) can be corrected by using a compliant waveform recognition (e.g., at 704) in order to improve the robustness of the medical indicators computed from PPG data (e.g., at 706).

It was noted that certain post-processing pipelines available at present implement computationally costly methods based on classical statistical methods, which may also show poor efficiency (see e.g., A. Reşit Kavsaoğlu, et al.: "Feature extraction for biometric recognition with photoplethysmography signals," 2013 21st Signal Processing and Communications Applications Conference (SIU); Chih-Chin Wu, et al.: "A wireless PPG signal processing system for long-term monitoring," 2016 IEEE International Conference on Consumer Electronics (ICCE); or Jia-Ju Liao, et al.: "An effective photoplethysmographic signal processing system based on EEMD method," VLSI Design, Automation and Test (VLSI-DAT), 2015).

This issue has been somehow addressed in the literature. For instance, S. K. Deric Tang, et al.: "PPG Signal Reconstruction using a combination of Discrete Wavelet Transform and Empirical Mode Decomposition"—2016 6th International Conference on Intelligent and Advanced Systems (ICIAS) or M. Raghuram, et al.: "Use of complex EMD generated noise reference for adaptive reduction of motion artifacts from PPG signals"—2016 International Conference on Electrical, Electronics and Optimization Techniques (ICEEOT) have proposed a reconstruction pipeline for PPG signal based on the use of discrete wavelet transform (DWT) in combination with EMD (empirical mode decomposition) methodology.

Other authors (see e.g., Fulai Peng, et al.: "Motion artifact removal from photoplethysmographic signals by combining temporally constrained independent component analysis and adaptive filter," Journal List Biomed Eng Onlinev. 13; 2014PMC4021027) have proposed a PPG signal processing pipeline based on the use of an independent component analysis algorithm combined with the use of adaptive filters.

Similarly, Yadhuraj S. R., et al.: "GUI creation for removal of motion artifacts in PPG signals"—2016 3rd International Conference on Advanced Computing and Communications Systems (ICACCS) or M. Raghuram et al., "A Novel Approach for Motion Artifact Reduction in PPG Signals Based on AS-LMS Adaptive Filter," IEEE Transactions on Instrumentation and Measurement (Volume: 61, Issue: 5, May 2012) propose a pipeline based on LMS (least mean square) adaptive filter for removing motion artifacts in PPG signal.

Still other approaches have been proposed such as S. K. Deric Tang et al. (already cited) or M. Raghuram, et al.: "Use of complex EMD generated noise reference for adaptive reduction of motion artifacts from PPG signals"—2016 International Conference on Electrical, Electronics, and Optimization Techniques (ICEEOT) which are based on the use of mathematical analysis and combined statistics in order to identify specific points in the standard PPG pattern have been proposed as well.

Alternatively, a full PPG signal analysis pipeline for pulse wave velocity (PWV) measurement as medical indicator for cardiovascular risk assessment has been considered (see e.g., D. Narayana Dutt, et al.: "Digital processing of ECG and PPG signals for study of arterial parameters for cardiovascular risk assessment"—2015 International Conference on Communications and Signal Processing (ICCSP).

In one or more embodiments a Laboratory Virtual Instrumentation Engineering Workbench (LabVIEW) software tool as available from National Instruments (NI) can be adopted in order to acquire PPG signals. Such a software tool can control a 24-bit ADC NI PXIe-4303 NI acquisition system (see e.g., 20) adapted for cooperating with a graphical user interface (GUI) as shown at 40A. The possibility also exists of comparing two PPG signals acquired from probes 10 arranged at different body sites and measuring the temporal delay between them. One or more embodiments may operate with a sampling frequency of 1 kHz, with data stored in a log file selectable by the user.

One or more embodiments may adopt e.g., MATLAB® toolboxes for implementing a processing pipeline as exemplified at 70 applied to collected PPG signals.

In one or more embodiments, the PPG raw signal filter block 702 may include e.g., a FIR pass-band scheme (low-pass filter plus high-pass filter) which facilitates a filter-assessment of the raw signal in relevant frequency ranges of the PPG waveform. In exemplary embodiments, the PPG raw signals from the SiPM-probes 10 can be filtered by using a finite impulse response (FIR) filter as available in the MATLAB® Filter Design & Analysis Tool (see also, e.g., Ifeachor E C, Jervis B W: "A framework for digital filter design; Finite impulse response (FIR) filter design" in Digital Signal Processing, Dagless E L, O'Reilly J, eds, Chaps 5, 6. Addison-Wesley, Woking, 1993; 251-73.

In such exemplary embodiments, the FIR filter is configured to remove the 50 Hz (or 60 Hz, depending in the country) power line frequency noise and other signal artifacts as well. The FIR coefficients can be obtained by using the EquiRipple method which facilitates avoiding phase distortion issues.

Figure 4:
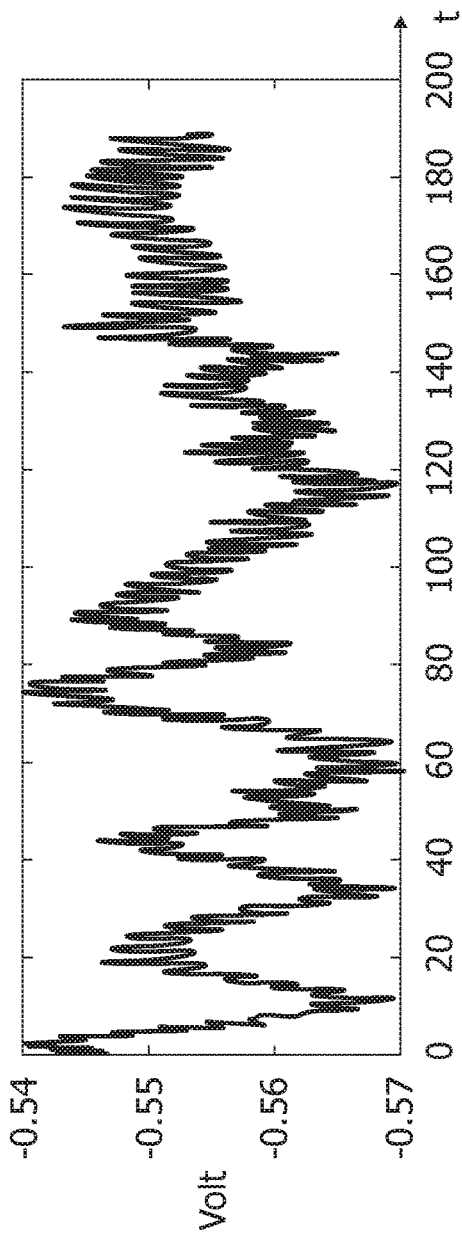
FIGS. 4 to 8 are diagrams exemplary of possible time behavior of certain signals in embodiments.

FIG. 4 is exemplary of a (pressure-wave free or pulse-wave free) wave pattern for PPG signal detection. The wave (ordinate scale in Volt and abscissa time scale in seconds) is characterized by a number of parameters like the width, the systolic peak, the dicrotic notch and the diastolic peak.

As otherwise known from the literature (see e.g., J. Allen, already cited) such a "standard" PPG waveform may in fact exhibit some differences in its pattern depending on the body-site (ears, fingers, toes) in which the signal is measured. For instance, PPG signals acquired at the left wrist, at the right wrist and at an ankle may exhibit differences which are maintained even after filtering and which are clearly observable in a filtered signal once zoomed.

In one or more embodiments filtering (e.g., at 702 in FIG. 3) can return a signal including PPG information and other low frequencies component, which are likely ascribable e.g., to respiration. It was otherwise observed that, e.g., in order to investigate the low frequency range, an IIR (infinite impulse response) filtering may be more convenient and efficient than FIR (finite impulse response).

A pattern recognition system (PRS) block as 704 in FIG. 3 may segment the whole PPG filtered time-series in order to analyze each single PPG waveform and facilitate understanding of the compliance of that waveform with respect to standard PPG pattern.

In one or more embodiments, a dynamical system can provide a time-based evolution of its variable close to the standard PPG waveform.

For instance, an autonomous nonlinear dynamic system (as disclosed e.g., in P. Arena, et al.: "A CNN-based chip for robot locomotion control," IEEE Transactions on Circuits and Systems, 2005, Volume: 52, Issue 9) may be expressed as:

$$\begin{cases} x_1' = -x_1 + (1+\mu)y_1 - \beta y_2 + \gamma_1 \\ x_2' = -x_2 + (1+\mu)y_2 - \beta y_1 + \gamma_2 \end{cases} \quad (1)$$

where:

$$y_j = \frac{1}{2}(|x_j + 1| - |x_j - 1|), j = 1, 2$$

and:

Such a nonlinear autonomous system can show different dynamics. In one or more embodiments the following set of parameters and initial conditions can be adopted:

$$\mu=0.5; \beta=1; \gamma_1=-0.3; \gamma_2=0.3; x_1(0)=0.15; x_2(0)=0.15;$$

A system according to (1) above may show a typical nonlinear biological reaction-diffusion system suited for managing locomotion in bio-inspired robots (see e.g., P. Arena et al., already cited). Each variable (x1 and x2) of the mathematical model in (1) represents so-called moto-neurons so that the evolution of each variable shows a biological dynamics as involved in locomotion of such biological species. A system according to (1) above can be used for generating complex dynamic phenomena adapted for use in controlling locomotion in bio-inspired robots (see again, e.g., P. Arena et al., already repeatedly cited). The set of system parameters discuses above was found to be suitable for defining a specific type of nonlinear dynamics (x2 variable) for the modelled reaction-diffusion process, which is close to a standard PPG time series.

The autonomous oscillator according to (1) above and configured with such parameters, shows a nonlinear steady-state autonomous oscillation for the variable x2 that is able to reproduce the behavior of the PPG dynamics.

If one considers the single waveform of that dynamics, after a normalization in the interval [0, 1] and resizing e.g., by means of the method proposed in Yadhurai S. R., et al. (already cited), a pattern that was found to be well adapted to be used as PPG reference wave generator for a pattern recognition system (PRS) block as 704 in FIG. 3.

A nonlinear system as expressed by the relationship (1) above can be also used as reference waveform for a modified version of PPG signal, usually referred to as "PPG with pressure wave."

By adopting this dynamics, a PRS block as 704 in FIG. 3 can perform a mathematical analysis of a computed approximation of the first and second derivatives of the PPG filtered signal. The possibility will also exist of identifying the interval (and related sample) in which the first derivative is zero, and ascertaining if the identified PPG peak is a maximum or minimum value for the waveform by analyzing the second derivative and the original PPG signal (in the neighborhood of interval in which first derivative is zero).

In one or more embodiments, the PRS block 704 may perform further global thresholds-based PPG data analysis aiming at avoiding local peaks and valleys (that is maximum and minimum). This kind of analysis can be extended to a whole PPG time-series and to each detected waveform.

In one or more embodiments, the PRS block 704 can perform a preliminary segmentation of the single PPG waveform e.g., by choosing each waveform between two valleys (minimum values).

The PPG segmented waveform obtained can be normalized and resized e.g., via a nearest algorithm (see e.g., F. Rundo, et al.: "Adaptive Learning for Zooming Digital Images"-ICCE 2007. Digest of Technical Papers. International Conference on Consumer Electronics, 2007) in order to make it comparable (in terms of value and as regards the time-axis) with a PPG reference waveform.

In one of more embodiments, a sample cross-correlation analysis with thresholds can then be performed by the PRS block 704 in order to study the similarity between the two time-series.

In one or more embodiments, a PPG waveform can be regarded as "compliant" if cross-correlation peaks and valleys (e.g., maximum and minimum cross-correlation values) lie within a range defined by specific thresholds as discussed previously. In one or more embodiments, non-compliant waveforms can thus be discarded and the compliant waveforms can be accepted for processing and presentation of results.

In one or more embodiments, a processing pipeline as exemplified in FIG. 3 can provide (e.g., at 706) an estimation of various medical indicators as needed for cardiovascular assessment stage such as A1, PWV, beats per minute (BPM) an so on: see e.g., M. Elgendi: "On the Analysis of Fingertip Photoplethysmogram Signals," Current Cardiology Reviews 2012, 8, 14-25.

One or more embodiments facilitate PPG wave recognition based on a processing pipeline configured for performing non-invasive estimation of useful medical indicators. One or more embodiments may rely on a processing pipeline composed by a PPG raw signal filter (e.g., 702 in FIG. 3) including an, e.g., FIR pass-band scheme (low-pass filter plus high-pass filter), a PPG pattern recognition system (e.g., 704), and one or more blocks (e.g., 706 and 708) for medical indicator detection and extraction.

The resulting processed PPG signal can support the diagnostic activity of a medical practitioner with a robust estimation of specific medical parameters correlated to main atherosclerotic pathologies such as artery stiffness, artery ageing, and arterial oxygen saturation.

One or more embodiments are adapted for use also with conventional (e.g., non-SiPM) PPG sensors. The use of SiPM sensors can be advantageous in various embodiments in view of the integration and miniaturization capabilities of SiPM sensors.

The following is a further detailed exemplary description of certain features of one or more embodiments.

As noted, FIG. 4 is a diagram exemplary of a the PPG detection waveform (raw data) which can be obtained with a PPG signal detection device including LEDs with specific wavelengths (usually infrared at 940 nm) and a SiPM photomultiplier of the type disclosed e.g., in the articles by M. Mazzillo, et al. already cited.

In such a device, light emitted by the LEDs is absorbed by the skin (DC component) and by the arteries, e.g., by oxygenated (and in small part by non-oxygenated) hemoglobin (AC component). Therefore, the residual reflected light (as resulting e.g., from back-scattering) will be proportional-differential with respect to the amount of light absorbed by the hemoglobin in the patient's blood in the various phases of the heart (systolic, diastolic, dicrotic, and so on). The (e.g., SiPM photomultiplier) PPG sensor will thus detect the presence of back-scattered photons (reflected light) by producing a corresponding electrical signal that can be sampled e.g., by 24-bit ADC (e.g., in the interface 10B of FIG. 2) thus providing a PPG signal as shown in FIG. 4.

Such a signal includes the DC and the AC components discussed above, as well as various types on measurement noise, e.g., electronic noise, noise due to power supply (e.g., 50 Hz or 60 Hz), noise due to movement of the patient's body, respiratory activity, and so on.

For most applications as considered in the foregoing, only the AC component of the PPG signal is helpful, the AC component lying e.g., in the 0.5-7.5 Hz frequency range.

One or more embodiments as exemplified may thus include a filtering system (e.g., 702 in FIG. 4) active (only) in that range. An otherwise conventional infinite impulse response (IIR) filter system including a low-pass filter (with cut-off e.g., at 7.21 Hz) and a high-pass filter (with cut-off e.g., at 0.5 Hz) is exemplary of such a filter.

Figure 5:
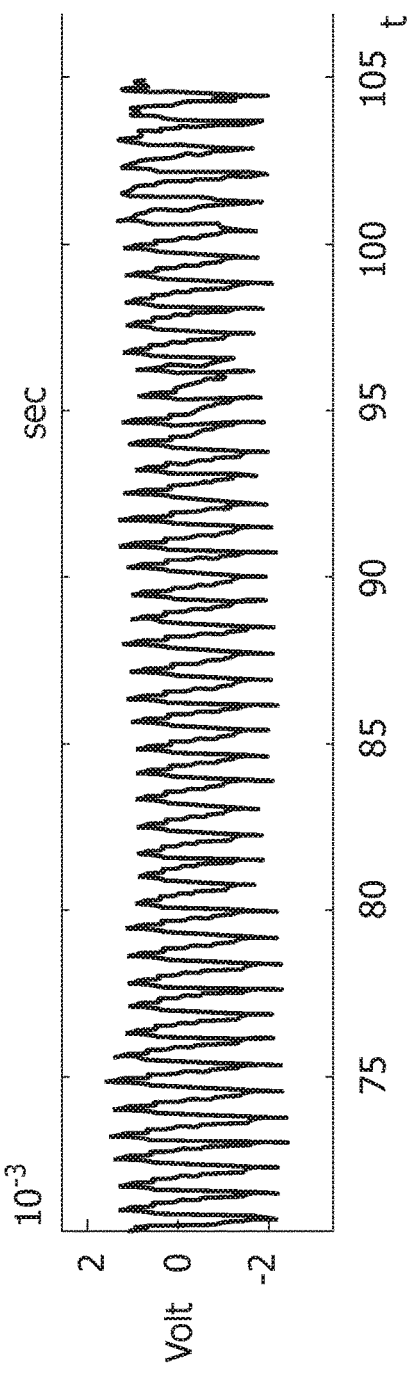

An example of a possible time behavior of a resulting filtered signal is reproduced in FIG. 5 (again Volt ordinate scale v. time abscissa scale in seconds).

The signal resulting from such filtering will not include only the patterns conforming to the classical form of a PPG signal: the signal resulting from such filtering may (also) include noisy patterns due e.g., to motion artifacts (such as artifacts resulting from small movements of the patient at the measurement sites). As noted, PPG signals can be sensed at plural points in the human body and therefore suffer from sampling site movement.

Figure 6:
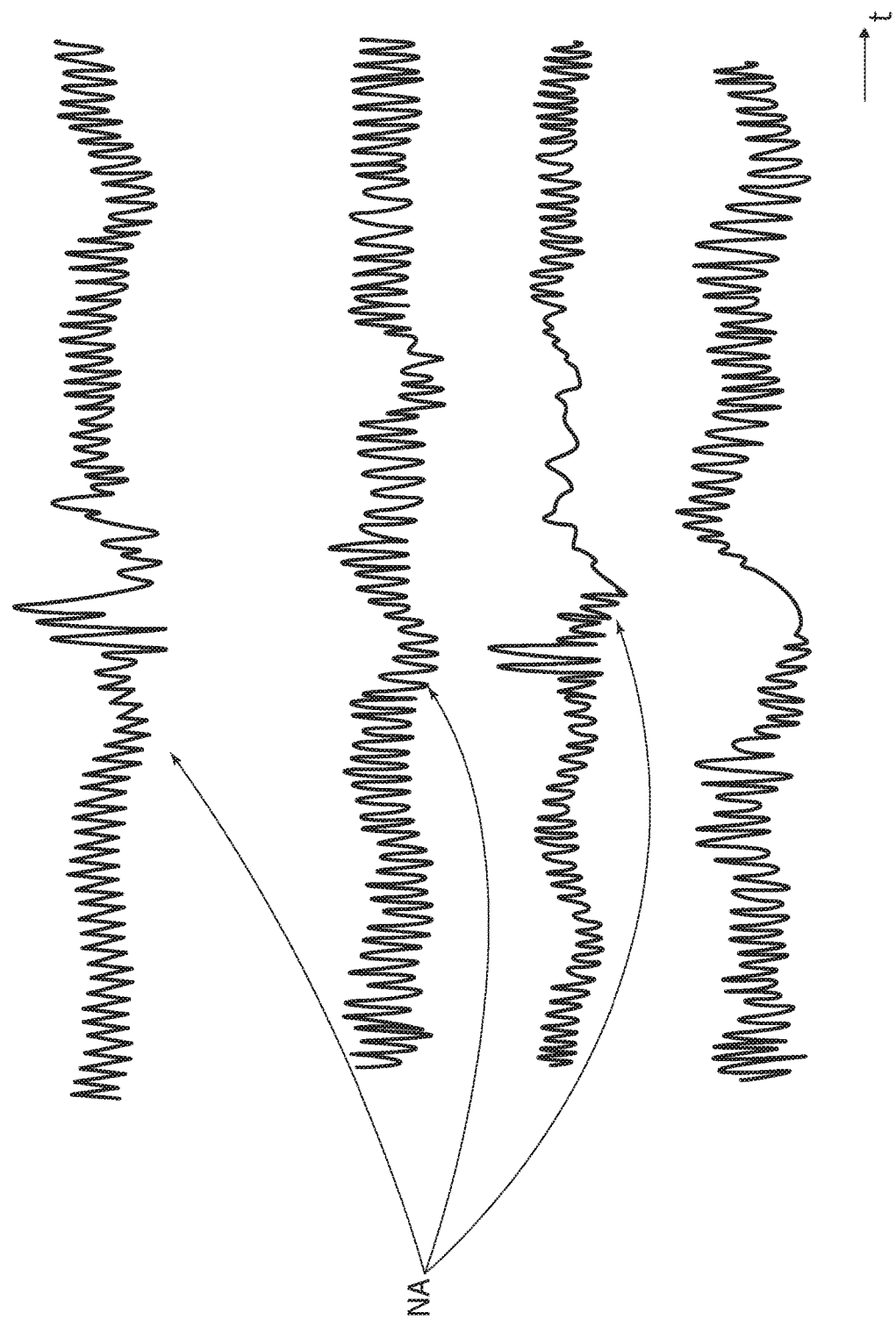

The diagrams of FIG. 6 are exemplary of possible noise and PPG artifacts NA which may affect the PPG signal even after filtering at 702.

In one or more embodiments, the processing pipeline 700 may include (see e.g., block 704 in FIG. 3) an automatic recognition system of a "correct" PPG pattern which is robust and fast in processing signals and in providing pattern recognition.

In one or more embodiments, such a system may rely on the concept of associating to the cardiovascular system (e.g., the systolic and diastolic phases) a reaction-diffusion process where e.g., the diastolic phase is associated with a reaction process and the systolic phase is associated with a diffusion process.

This may occur on the basis of the model already discussed in the foregoing which in one or more embodiments is used to emulate such a physiological process in the form:

$$\begin{cases} \frac{\partial x_1(t)}{\partial(t)} = -x_1(t) + (1+\mu)y_1(t) - \beta y_2(t) + \gamma_1 \\ \frac{\partial x_2(t)}{\partial(t)} = -x_2(t) + (1+\mu)y_2(t) - \beta y_1(t) + \gamma_2 \end{cases}$$

$$y_j = \frac{1}{2}(|x_j + 1| - |x_j - 1|)j$$

where, for example, $$\mu=0.5; \beta=1; \gamma_1=-0.3; \beta_2=0.3; x_1(0)=0.15; x_2(0)=0.15$$

As noted (see, P. Arena et al., already repeatedly cited), an exemplary system as expressed by the relationships above shows a typical nonlinear biological reaction-diffusion system of partial differential equations (PDEs) which is suited for managing locomotion in bio-inspired robots. Each variable ($x_1$ and $x_2$) in such a mathematical model can be regarded as representative of so-called moto-neurons so that the evolution of each variable shows a biological dynamics as involved in locomotion of such biological species. A system according to the relationship above, once properly coupled, can be used for generating complex dynamic phenomena suitable for control the locomotion in bio-inspired robots. The set of exemplary system parameters discussed above was found to be useful in defining a specific type of nonlinear dynamic (x2 variable), for the modelled reaction-diffusion process, which is close to a standard PPG time series.

In that way, a "bio-inspired" mathematical analytic model of PPG waveform can be produces which facilitates careful study and analysis of the PPG features. As in the case of locomotion control in bio-inspired robots, such a mathematical can be configured by changing the set of parameters discussed above in order to produce modified biological signals (both for $x_1$ and $x_2$ variable) which can be used in modelling different types of PPG patterns as conventionally detected at different sampling-points in the human body (ear, thumb, toe, etc. . . . ).

Figure 7:
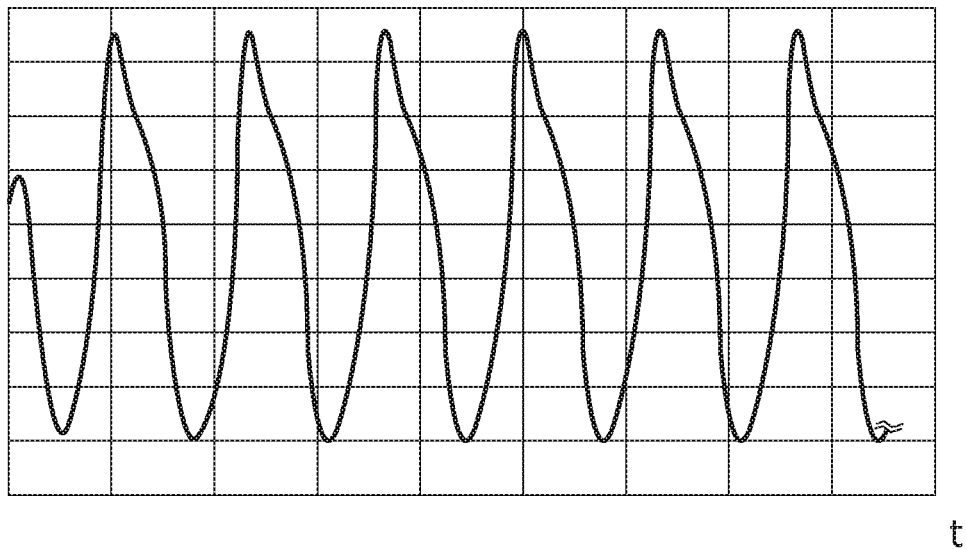

The above nonlinear system, as configured above, may have a limit cycle where it will oscillate as shown in FIG. 7.

Figure 8:
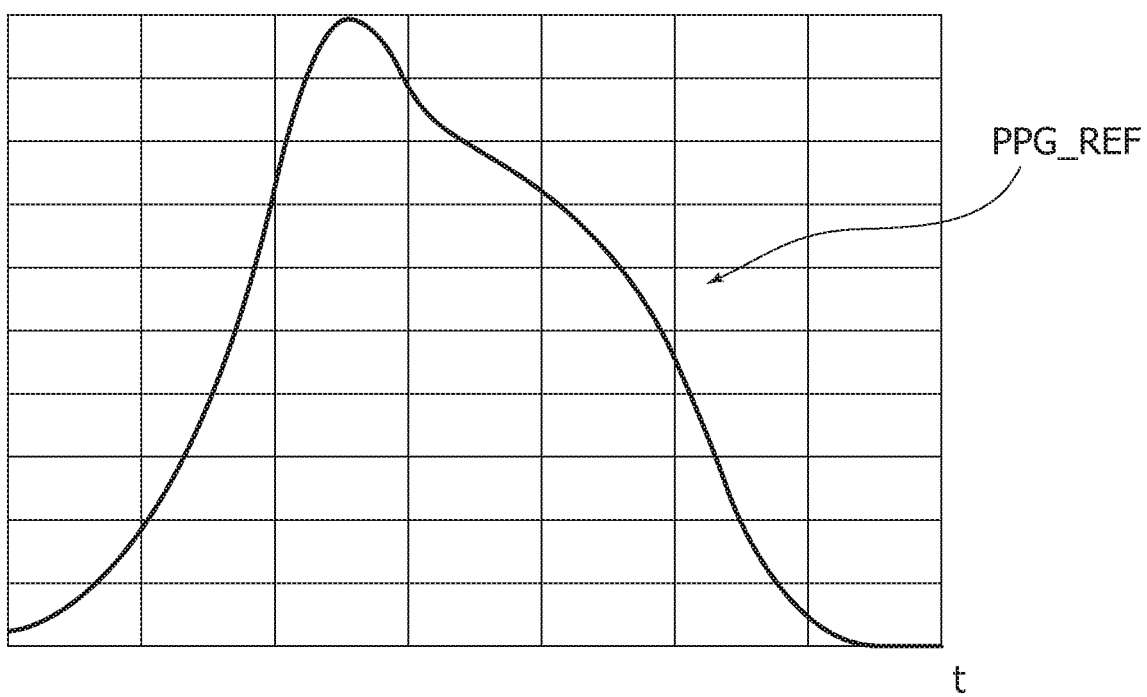

By considering only transient dynamics, a single waveform will result which, once possibly normalized, may be as shown in FIG. 8, that is, a waveform adapted to be used as a reference pattern in the pattern recognition block 704 of FIG. 3.

The model discussed in the foregoing can be implemented using cellular neural network (CNN) technology, thus offering high-speed computing speeds.

One or more embodiments may adopt an analog implementation of CNNs as disclosed e.g., in P. Arena, et al. (already cited). Such an implementation, as exemplified in FIG. 9 corresponds to the analytic and circuit model of a CNN which can be expressed as:

$$C\frac{dv_{xij}(t)}{dt} = -\frac{1}{Rx} \cdot v_{xij}(t) +$$

$$\sum_{C(k,l) \in Nr(i,j)} A(i, j; k, l) \cdot v_{ykl}(t) + \sum_{C(k,l) \in Nr(i,j)} B(i, j; k, l) \cdot v_{ukl}(t) +$$

$$\sum_{C(k,l) \in Nr(i,j)} C(i, j; k, l) \cdot v_{xkl}(t) + I(1 \le i \le M, 1 \le j \le N)$$

$$Nr(i, j) = C(k, l)$$

$$v_{yij}(t) = \frac{1}{2}(|v_{xij}(t) + 1| - |v_{xij}(t) - 1|) \quad (\max(|k - i|, |l - j|) \le r,$$

$$(1 \le i \le M, 1 \le j \le N) \quad 1 \le k \le M, 1 \le l \le N)$$

$$I_{xy}(i, j; k, l) = A(i, j; k, l)v_{ykl}$$

$$I_{xu}(i, j; k, l) = B(i, j; k, l)v_{ukl}.$$

Cellular Neural Networks (Cellular Nonlinear Networks) or CNNs are arrays of nonlinear and simple computing elements characterized by local interactions between cells. A CNN paradigm is thus well suited to describe locally interconnected simple dynamical systems showing a lattice-like structure. CNNs are conventionally used for various types of applications such as image and signal processing, bio-inspired system modelling, or high-speed resolution of partial differential equations (PDEs). This may be particularly the case when the emulation of solutions of PDEs involves considering of the evolution of each variable over time, its position (in space) and its interactions deriving from the space-distributed structure of the whole system (indeed, the numerical solution of PDEs almost inevitably involves spatial discretization).

The CNN paradigm thus represents a helpful tool in the real-time simulation of spatio-temporal phenomena as the PDEs in the reaction-diffusion model considered herein, thus giving rise to reaction-diffusion Cellular Neural Networks (Cellular Nonlinear Networks) or RD-CNNs suited for solving RD PDEs as discussed previously.

Further aspects of such CNNs are presented e.g., in P. Arena et al., already cited, and the reference mentioned therein, where e.g., VLSI high-speed implementation of such RD-CNNs is discussed.

One or more embodiments may adopt RD-CNNs including a single 1D layer of coupled cells. While conventional hardware realization of RD-CNNs may involve an 8×1 1D layer of cells, one or more embodiments may use a 1D layer of 4×1 properly coupled cells.

Figure 9:
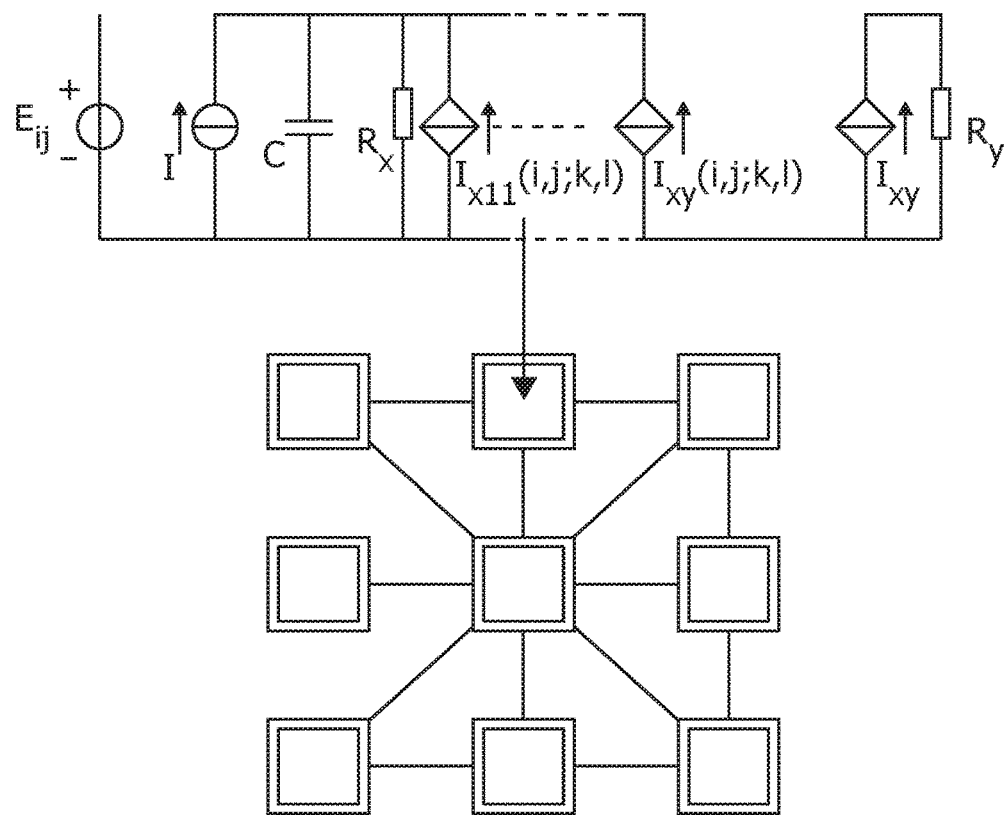
FIG. 9 is exemplary of the possible layout of a neural network in embodiments.

The dynamics of a CNNs cell C(i,j) as exemplified in FIG. 9 is described by the equations reported above where the state of the cell is represented by capacitor voltage ($v_{xij}$) while input and output of the neighborhood coupled cells is represented by the voltages "$v_{ukl}$" and "$v_{ykl}$," respectively. The neighborhood of single cell C(i,j) is mathematically represented by Nr(i,j) while the type of cell-coupling is defined by the elements of the so-called cloning matrix templates A(I,j;k,l), B(I,j;k,l), C(I,j;k,l) as well as by the bias I.

The output voltage of single cell "$v_{yij}(t)$" is defined by Piece-Wise Linear (PWL) remapping of the state of the cell C(i,j). A VLSI implementation of CNNs involving so-called State-Controlled CNNs (SC-CNNs), where a C(I,j;k,l) matrix template is added allows high-speed computation of single cell dynamic which, in one or more embodiments, consists in $x_1$ and $x_2$ dynamics of the RD PDE system as per mathematical model discussed above.

Figure 10:
FIGS. 10 to 12 are exemplary of possible processing of certain signals in embodiments.
Figure 11:
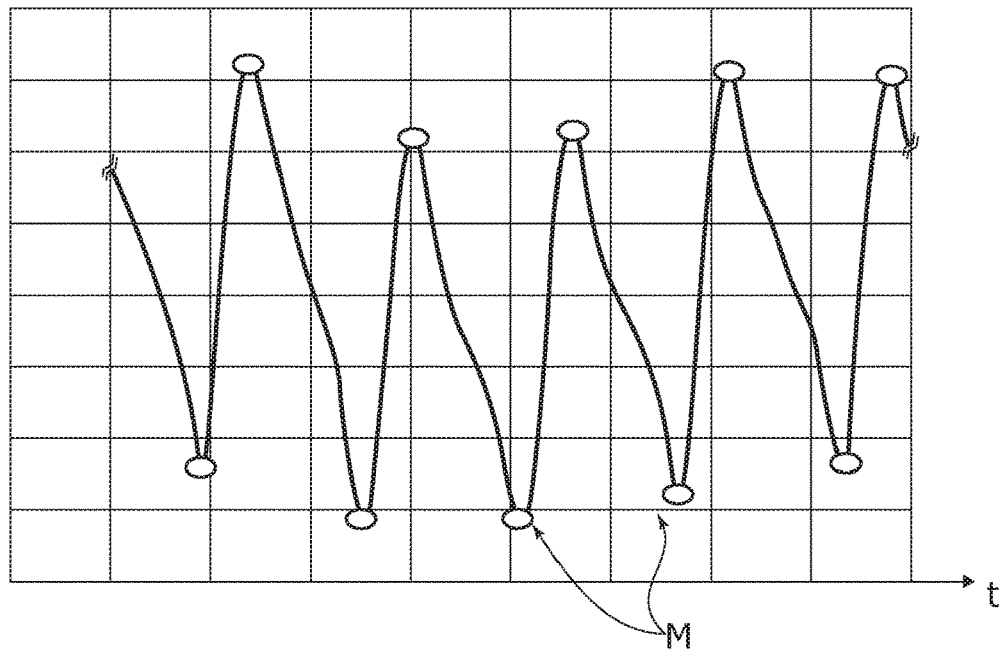
Figure 12:
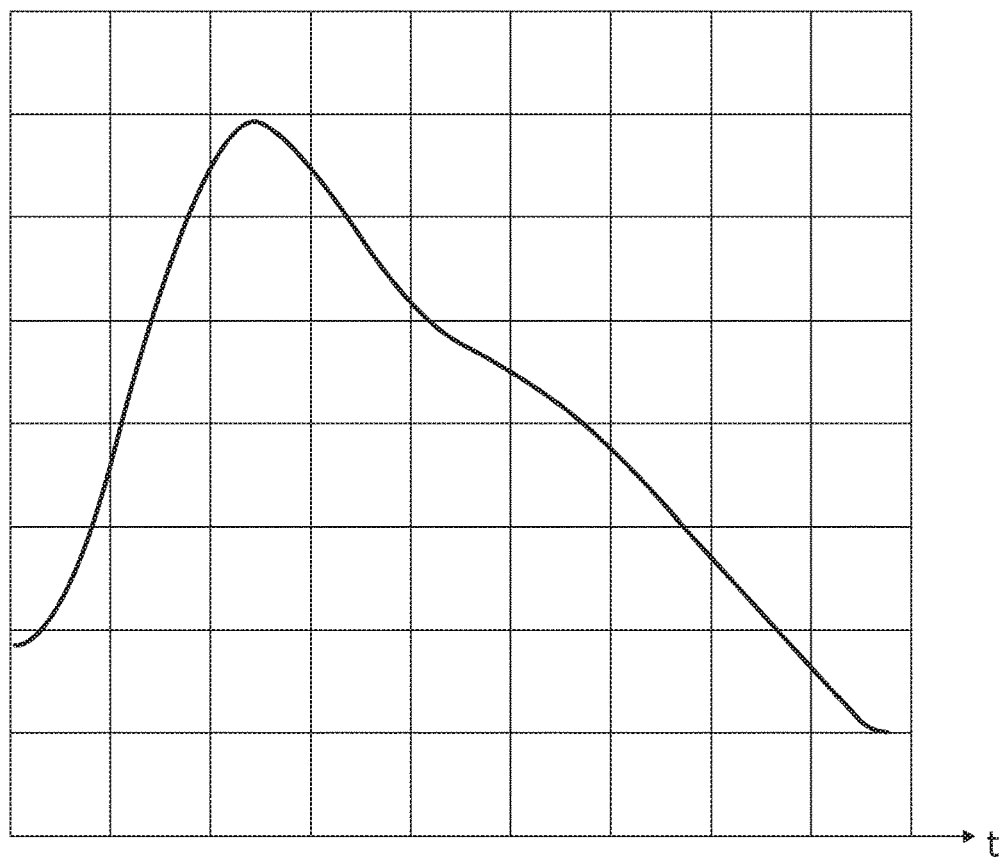
Figure 13:
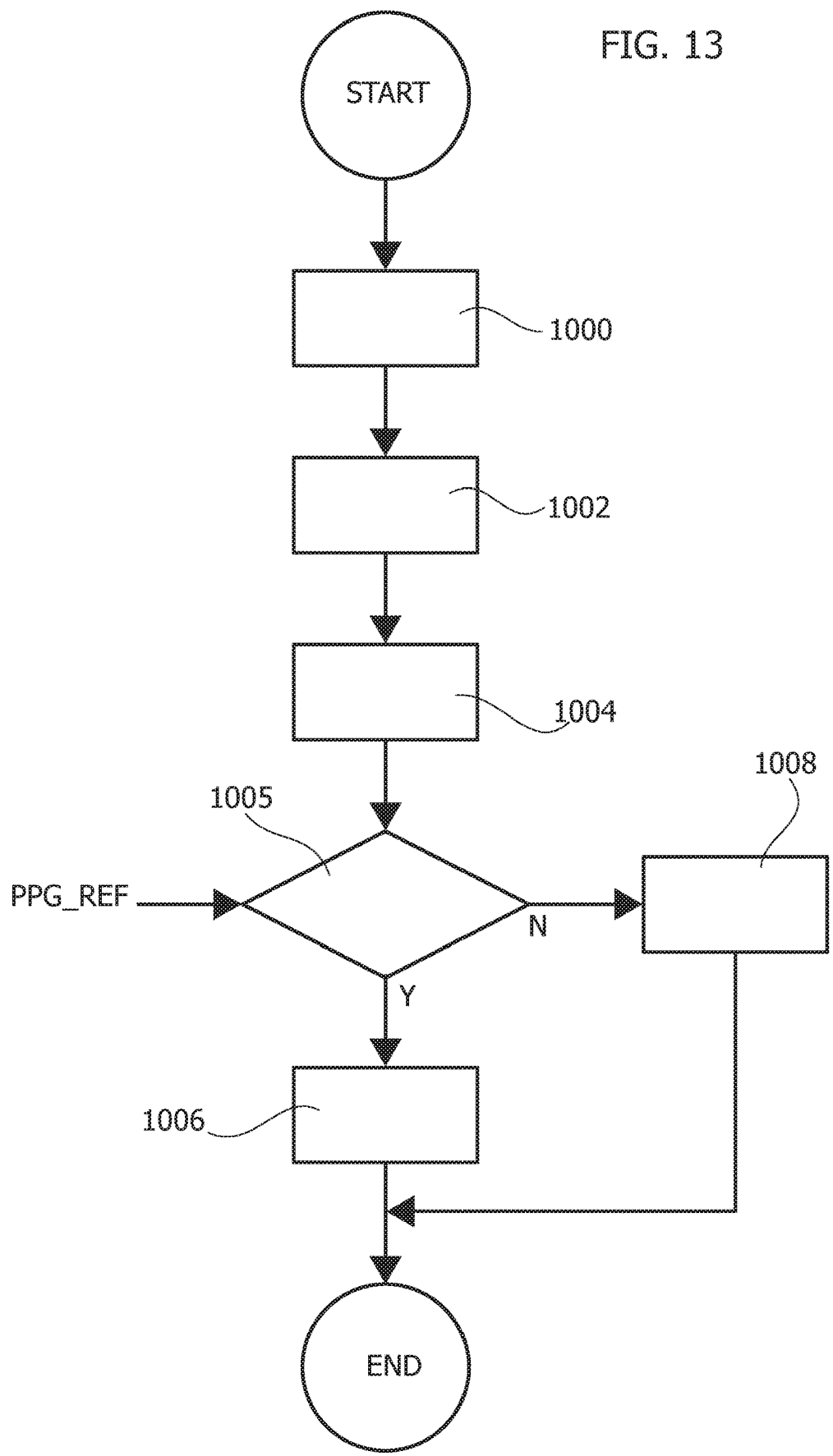
FIG. 13 is a flow chart exemplary of possible processing acts in embodiments.

Thus, the PPG signal acquired and filtered (e.g., 702) as described above will be preliminarily segmented as exemplified in FIGS. 10 to 12 and in the flow-chart of FIG. 13. This may involve e.g., calculating the first and second derivatives of the (filtered) PPG signal (step 1000 in FIG. 13), that is:

$$\frac{\partial PPG(t)}{\partial t} \to \frac{PPG(t_k + h) - PPG(t_k)}{h}$$

$$\frac{\partial^2 PPG(t)}{\partial t^2} \to \frac{PPG(t_k + h) - 2PPG(t_k) + PPG(t_k - h)}{h^2}$$

In that way the peaks and valleys (maximum and minimum points) will be found throughout the acquired time series as schematically shown in FIG. 11 (step 1002 in FIG. 13).

Having the valleys (minimum points) M of the sampled and filtered PPG signal, the pattern recognition system 704 will be able to find a "correct" PPG pattern between two valleys (step 1004 in FIG. 13). Segments of the acquired PPG signal may thus be taken as the waveforms between two valleys (minima) M and compared (step 1005 in FIG. 13) with the PPG pattern reference of FIG. 8 generated as PPG_REF by the nonlinear diffusion reaction system discussed above.

In one or more embodiments, the comparison can be made after formatting along the temporal and normalized axis between [0,1] both the PPG reference pattern and the segmented signal from the original signal, so that a homogeneous comparison is made. An exemplary algorithm for signal and image rescaling suited for that purpose is discussed e.g., in F. Rundo, et al. (already cited).

In one or more embodiments, the comparison can be made through a cross-correlation analysis between the two PPG patterns, as illustrated above.

For instance, all segmented PPG patterns with a sample cross-correlation (normalized over [0,1]) equal to 0.90 or higher will be considered for inclusion in the "correct" PPG signal (step 1006 in FIG. 13). Conversely, PPG patterns with a cross-correlation less than e.g., 0.90 will be discarded (step 1008 in FIG. 13) as they are considered distorted.

Such an approach facilitates obtaining at the end of the process (END in FIG. 13) a clean PPG signal without distortion or artifacts, by using a system capable of performing the related processing in real time e.g., via a CNN implementation of the PPG reference system.

Figure 14A:
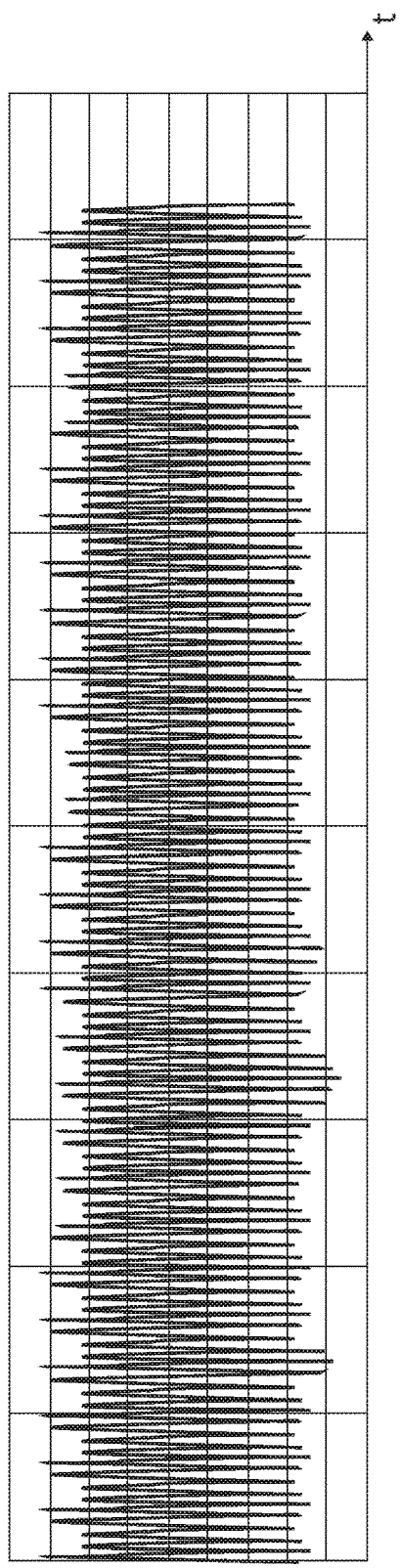
FIGS. 14A and 14B, respectively, are exemplary of possible time behavior of certain signals in embodiments.
Figure 14B:
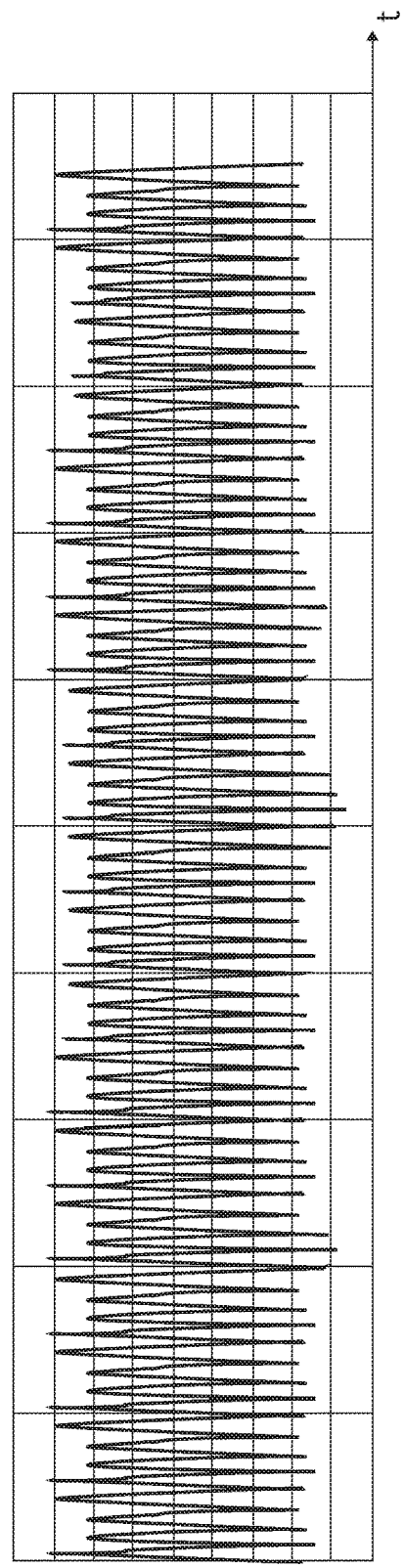

FIGS. 14A and 14B are representative of the possible time behavior, over a common abscissa time scale and with corresponding (arbitrary) ordinate scales of two signal corresponding to the "original" PPG signal as input to the processing discussed above—upper diagram, portion "a);" and the "clean" PPG signal resulting from processing discussed above—lower diagram, portion "b)."

Due to the non-compliant waveforms being discarded, the clean signal will include fewer waveforms with respect to the original signal, however with undesired distortion and artifacts removed from the waveforms retained in the clean signal.

In one or more embodiments (e.g., certain medical systems or systems for use in the automotive field as repeatedly discussed in the foregoing) such a clean PPG system can be used as such (e.g., by being in some form presented and/or used for various purposes).

In one or more embodiments such a clean PPG signal (obtained e.g., as discussed in the foregoing or otherwise) can be presented e.g., at 40C and/or be exploited in conjunction with the ECG signal from the probes 12, for instance for "validating" the ECG signal as a result of the ECG signal being found consistent (compliant) with the PPG signal.

To some extent, such an approach, providing for validation of an ECG signal based on a PPG signal (as possibly resulting from processing as discussed in the foregoing), can be regarded as alternative or complementary to ballistocardiography.

A ballistocardiograph (BCG) is a device capable of measuring ballistic forces on the heart.

Ballistocardiography is a technique for producing a graphical representation of repetitive motions of the human body arising from the sudden ejection of blood into the great vessels at each heartbeat. It is a vital sign in the 1-20 Hz frequency range caused by the mechanical movement of the heart and can be recorded by noninvasive methods from the surface of the body. The effect of main heart malfunctions can be identified by observing and analyzing the BCG signal.

One or more embodiments as exemplified herein are based on the recognition that, as exemplified in FIGS. 15A and 15B, an observable cross-correlation exists between the first-derivative of a PPG processed waveform (FIG. 15A) and ECG signal (FIG. 15B) for a same patient.

One or more embodiments, as exemplified in FIG. 1, may thus include the processing system (pipeline) 80 configured to operate on the (clean) PPG signal from the system 70 and on a corresponding ECG signal from the probes 12 as received from the acquisition instrumentation block 20 ("raw data" 50).

In one or more embodiments, as exemplified in FIG. 1, the processing system 80 may include a number of processing modules/circuits such as:

a block 801 configured for making available an ECG reference signal (for instance this may be a conventional ECG standard pattern stored in the ECG/PPG system or possibly loaded on-demand);

a block 802 configured for calculating a first-derivative PPG waveform for use in analyzing the related ECG waveform;

a block 803 configured for calculating a degree of cross-correlation of the first-derivative PPG waveform and the related ECG waveform;

a block 804 configured for calculating a degree of cross-correlation between the ECG reference signal waveform with the (detected) ECG waveforms to be analyzed;

a "validation" block 805 (here exemplified merely as a logical AND gate) sensitive to the outputs from the blocks 803 and 804 reaching certain threshold values (e.g., higher or equal to the certain threshold value).

In one or more embodiments, the outputs from the blocks 803 and 804 reaching certain threshold values may be indicative of the quality of the sampled ECG waveforms being adequate to permit the EGC signal to be regarded as a valid one, adapted to be reliably used for diagnostic purposes by a practitioner e.g., by being presented (displayed and/or printed) at 40C. This may occur as a result of validation signal V issued from the block 805.

One or more embodiments, as exemplified herein, may thus rely on a sort of "double check" involving both first-derivative PPG cross-correlation block (block 803) and ECG standard pattern cross-correlation (block 804) analysis which facilitates a high degree of reliability.

Those of skill in the art will otherwise appreciate that certain simplified embodiment may involve only one of the cross-correlation analysis acts/blocks discussed previously.

In one or more embodiments, bandpass filtering can be applied to the ECG signal for use in the block 804.

In one or more embodiments, such filtering of the ECG signal may be essentially similar to filtering applied to the PPG signal in block 702 as described previously (e.g., a low-pass section and high-pass section) save for a possible different choice of the cut-off frequencies (e.g., 0.5 Hz and 20 Hz for the ECG signal).

Figure 16:
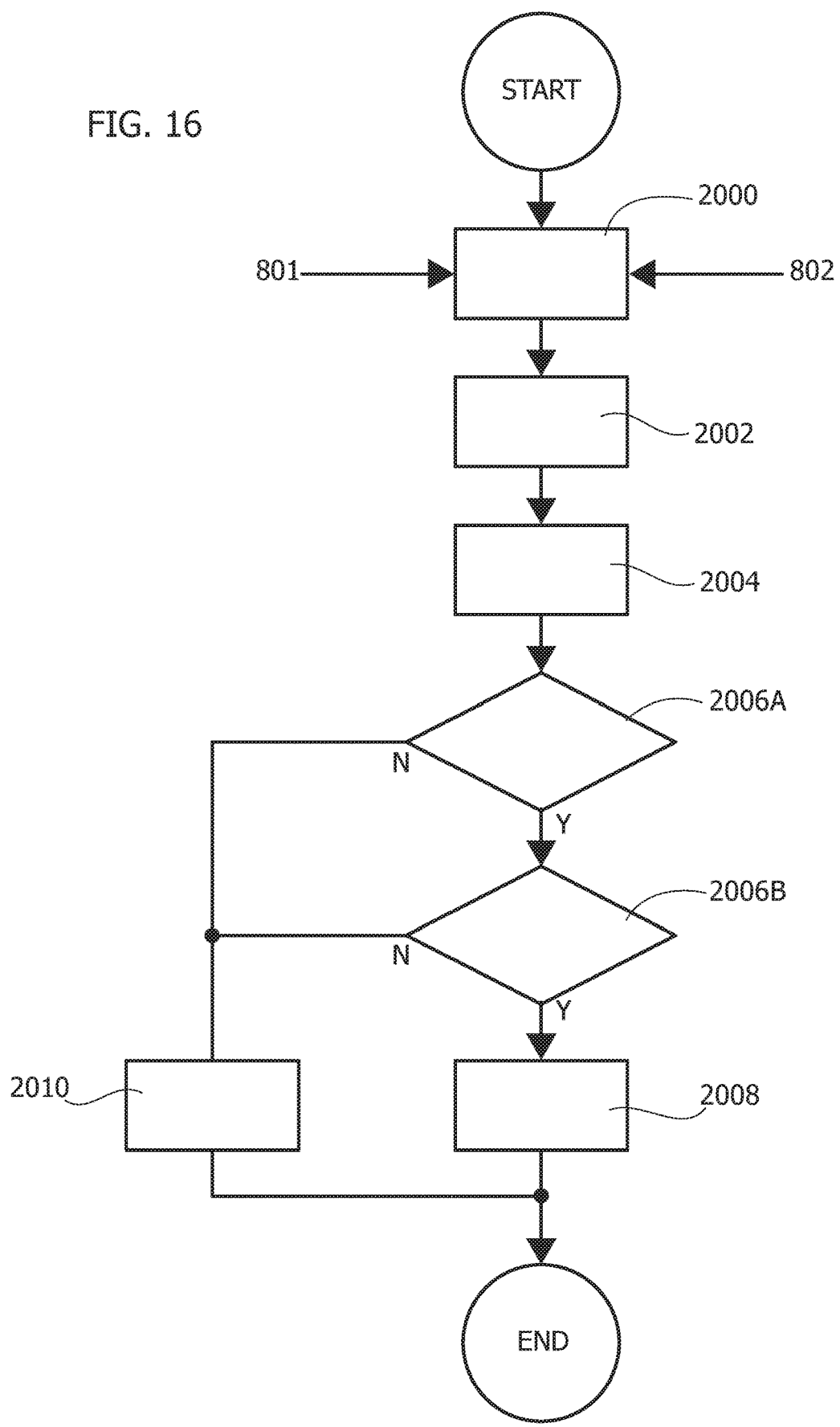
FIG. 16 is a flow chart exemplary of possible processing acts in embodiments.

The flow-chart of FIG. 16 is exemplary of possible processing of the ECG signals and the PPG derivative signal from the blocks 801 and 802 in the blocks 803 and 804, so that e.g., the compliant first-derivative PPG waveform from block 802 can be used for analyzing a related ECG waveform obtained by automatic segmentation of pre-filtered ECG from the block 801 in the same PPG time onset.

For that purpose, e.g., first-derivative PPG and the ECG waveforms can be normalized over the interval [0, 1] in a step 2000.

Time-rescaling may be performed in a step 2002 in order to time-align the peaks of the various signals involved e.g., the ECG waveforms and the first-derivative PPG, and the ECG waveforms and the ECG reference waveform.

This may involve e.g., a time-shift applied to the ECG signals based on a relationship such as:

$$ECG^j(t_k) -> ECG^j(t_k + \delta_k^j) \forall\ j = 1\ ...\ N$$

$$\forall\ t_k$$

$$N = \text{Number of } ECG \text{ waveform(s)}$$

In that way, cross-correlation analysis of these signals in a step 2004 can be facilitated by relying on time alignment (overlap) of the respective peaks.

Various known approaches can be used for that purpose. For instance, as discussed previously with respect to processing the PPG signal in the system 70, a "nearest" algorithm can be used to obtain time-comparable waveforms.

In that way a standard sample cross-correlation analysis can be finally performed in step 2004 to generate respective cross-correlation scores (indexes) e.g., between rescaled-normalized ECG waveforms and first-derivative PPG waveforms and a standard ECG reference pattern.

The scores thus obtained can then be compared with reference cross-correlation thresholds in steps 2006A and 2006B.

More details on cross-correlation procedures adapted for use in the cross-correlation acts discussed throughout this disclosure can be found e.g., in G. E. P. Box, G. M. Jenkins, and G. C. Reinsel, "Time Series Analysis: Forecasting and Control" John Wiley & Sons, Hoboken, N.J., 4th edition, 2007—Cap. 12 pag. 473-501.

Stated otherwise, one or more embodiments may involve:

"translating" (shifting in time) the sampled ECG waveforms to be analyzed by causing their peaks (maxima) to correspond with the peaks in the first-derivative PPG signal and the peak of the ECG reference signal, calculating (e.g., on signals normalized over the interval [0, 1]) cross-correlations between these signals, that is between:

i) the sampled ECG waveforms and the first-derivative PPG signal;

ii) the sampled ECG waveforms and the ECG reference signal;

comparing the cross-correlation indexes or scores with established compliance thresholds (identical values of 0.80 were found to represent a reasonable choice for both thresholds. Of course, different thresholds and different values can be used in one or more embodiments);

those analyzed ECG patterns having a cross-correlation indexes or scores reaching these thresholds (e.g., a cross-correlation equal to 0.80 or higher in both checks 2006A and 2006B (first-derivative PPG and ECG standard, respectively) will be considered a "conforming" ECG pattern to be retained (step 2008); otherwise they will be discarded (step 2010).

The blocks 2008 and 2010 in FIG. 16 are thus generally exemplary of operation of the block 805 in FIG. 1 as discussed previously, e.g.:

a validation signal V is issued at 2008 if both thresholds are reached (e.g., output "YES" from both steps 2006A and 2006B) so that ECG waveforms showing high cross-correlation with PPG-derivative waveforms and ECG reference waveform are "validated" e.g., for diagnostic purposes, ECG waveforms showing low correlation with either one of the PPG-derivative waveform or the ECG reference waveform (e.g., output "NO" from either one of steps 2006A and 2006B) are discarded at 2010 so that only "compliant" collected ECG waveforms can be used as a reference pattern for subsequent ECG analysis.

While per se not mandatory, such a "double check" of the ECG signal was found to facilitate providing reliable results with the former check (correlation with PPG-derivative) providing validation "as to form" and the latter check (correlation with ECG reference) providing validation "as to value/content."

In one or more embodiments, a method includes:

collecting (e.g., 10, 20) a PhotoPlethysmoGraphy, briefly PPG, signal, processing (e.g., 70) the PPG signal collected, wherein processing includes:

detecting (see e.g., 1002 and FIG. 11) peaks and valleys in the PPG signal, segmenting (e.g., 1004) the PPG signal to provide a time series of PPG waveforms located between two subsequent valleys in the PPG signal, applying (e.g., 706) to the waveforms in the time series pattern recognition (e.g., 1005) with respect to a reference PPG waveform pattern (PPG_REF, see e.g., FIG. 8) produced based on a mathematical model of the PPG signal by assigning to the waveforms in the time series a recognition score, and producing a resulting PPG signal by:

i) retaining (e.g., 1006) those waveforms in the time series having a recognition score reaching (e.g., 1005) a recognition threshold, and ii) discarding (e.g., 1008) those waveforms in the time series having a recognition score failing to reach the recognition threshold.

In one or more embodiments, processing the PPG signal collected may include (preliminary) bandpass filtering (e.g., 702) the PPG signal collected, optionally by joint low-pass and high-pass filtering.

In one or more embodiments, detecting said peaks and valleys (maxima and minima) may include calculating (e.g., 1000) first and second derivatives of the PPG signal.

One or more embodiments may include normalizing to a unitary range the PPG signal prior to said segmentation.

One or more embodiments may include producing the reference PPG waveform via a self-adaptive nonlinear oscillator.

One or more embodiments may include producing the reference PPG waveform with a reaction-diffusion model, with the diastolic and the systolic phases of the heart coupled with the reaction and diffusion properties of the reaction-diffusion model.

One or more embodiments may include producing the reference PPG waveform with a neural network (see e.g., FIG. 9).

One or more embodiments may include rescaling over time the reference PPG waveform pattern to facilitate applying pattern recognition to time-comparable waveforms.

In one or more embodiments pattern recognition may include cross-correlation analysis between the waveforms in the time series and the reference PPG waveform pattern, wherein the recognition score may include a cross-correlation index.

One or more embodiments may include:

collecting (e.g., 12, 20), together (e.g., simultaneously with the PPG signal collected), a time series of ElectroCardioGraphy (ECG) signal waveforms, calculating (e.g., 802) the first derivative of the PPG signal resulting from the processing (e.g., 70) of the PPG signal collected, performing (e.g., 803, 2004) cross-correlation of the ECG signal waveforms collected and the first derivative of the resulting PPG signal by assigning to the ECG signal waveforms collected cross-correlation scores with the first derivative of the resulting PPG signal, comparing (e.g., 2006A) with a validation threshold the cross-correlation scores of the ECG signal waveforms, and validating (e.g., 805, 2008) as valid ECG signal waveforms those ECG signal waveforms having cross-correlation scores reaching the validation threshold.

One or more embodiments may include:

performing (e.g., 804, 2004) cross-correlation of the ECG signal waveforms collected and an ECG reference waveform (e.g., 801) by assigning to the ECG signal waveforms collected further cross-correlation scores with the ECG reference waveform, comparing (e.g., 2006B) with a further validation threshold the further cross-correlation scores of the ECG signal waveforms, and validating (e.g., 805, 2008) as valid ECG signal waveforms those ECG signal waveforms having both said cross-correlation scores reaching the validation threshold (2006A) and said further cross-correlation scores reaching the further validation threshold (2006B).

One or more embodiments may include bandpass filtering (e.g., at 801) the ECG signal waveforms collected, optionally by joint low-pass and high-pass filtering, e.g., with cut-off frequencies different from those used for bandpass filtering the PPG signal.

In one or more embodiments, a system may include:

a collection circuit block (e.g., 20) for receiving a PPG signal collected, a processing circuit (e.g., 60) coupled to the collection circuit block to receive therefrom the PPG signal collected, the processing circuit configured for processing the PPG signal collected with the method of one or more embodiments.

One or more embodiments may include:

the collection circuit block configured for receiving, together with said PPG signal collected, a time series of ElectroCardioGraphy (ECG) signal waveforms, the processing circuit coupled to the collection circuit block to receive therefrom the PPG signal collected as well as a time series of ECG signal waveforms, the processing circuit configured for processing the PPG signal collected and the ECG signal waveforms with the method of one or more embodiments.

One or more embodiments may include a computer program product loadable in the memory of at least one processing circuit (e.g., 60) and including software code portions for executing the steps of the method of one or more embodiments when the product is run on at least one processing circuit.

Without prejudice to the underlying principles, the details and embodiments may vary, even significantly, with respect to what has been described by way of example only, without departing from the extent of protection. The extent of protection is defined by the annexed claims.

What is claimed is:

1. A method comprising:
   receiving a photoplethysmography (PPG) signal collected by a PPG sensing apparatus;
   detecting peaks and valleys in the PPG signal;
   segmenting the PPG signal to provide a first time series of PPG waveforms located between two subsequent valleys in the PPG signal;
   applying pattern recognition to the first time series with respect to a reference PPG waveform pattern produced based on a mathematical model of the PPG signal by assigning a recognition score to the waveforms in the first time series, wherein the reference PPG waveform pattern is produced with a reaction-diffusion model, with diastolic and systolic phases of a heart coupled with the reaction and diffusion properties of the reaction-diffusion model, and wherein applying the pattern recognition comprises applying cross-correlation analysis between the waveforms in the first time series and the reference PPG waveform pattern;
   retaining the waveforms in the first time series having a recognition score higher or equal to a recognition threshold; and
   discarding the waveforms in the first time series having a recognition score lower than the recognition threshold thereby producing a resulting PPG signal.

2. The method of claim 1, further comprising bandpass filtering the PPG signal.

3. The method of claim 2, wherein bandpass filtering the PPG signal comprises a joint low-pass and high-pass filtering.

4. The method of claim 1, wherein detecting the peaks and valleys comprises calculating first and second derivatives of the PPG signal.

5. The method of claim 1, further comprising normalizing the PPG signal to a unitary range prior to the segmenting.

6. The method of claim 1, further comprising producing the reference PPG waveform pattern via a self-adaptive nonlinear oscillator.

7. The method of claim 6, wherein the reference PPG waveform pattern is produced with a neural network.

8. The method of claim 1, further comprising rescaling the reference PPG waveform pattern over time to facilitate applying pattern recognition to time-comparable waveforms.

9. The method of claim 1, wherein the recognition score includes a cross-correlation index.

10. The method of claim 1, wherein receiving the PPG signal further includes receiving a second time series of electrocardiography (ECG) signal waveforms, the method further comprising:
    calculating a first derivative of the resulting PPG signal;
    performing cross-correlation of the ECG signal waveforms and the first derivative of the resulting PPG signal by assigning to the ECG signal waveforms cross-correlation scores with the first derivative of the resulting PPG signal;
    comparing with a validation threshold the cross-correlation scores of the ECG signal waveforms; and
    validating as valid ECG signal waveforms the ECG signal waveforms having cross-correlation scores higher or equal to the validation threshold.

11. The method of claim 10, further comprising:
    performing cross-correlation of the ECG signal waveforms and an ECG reference waveform by assigning, to the ECG signal waveforms, second cross-correlation scores with the ECG reference waveform;
    comparing with a second validation threshold the second cross-correlation scores of the ECG signal waveforms; and
    validating as valid ECG signal waveforms the ECG signal waveforms having both the cross-correlation scores higher or equal to the validation threshold and the second cross-correlation scores higher or equal to the second validation threshold.

12. The method of claim 10, further comprising bandpass filtering the ECG signal waveforms.

13. The method of claim 1, wherein the PPG sensing apparatus comprises a plurality of probes and a front-end device and wherein receiving the PPG signals comprises performing measurements using the probes and receiving measurement information from the front-end device.

14. A method comprising:
    receiving a photoplethysmography (PPG) signal collected by a PPG sensing apparatus;
    detecting peaks and valleys in the PPG signal;
    segmenting the PPG signal to provide a first time series of PPG waveforms located between two subsequent valleys in the PPG signal;

producing a reference PPG waveform pattern based on a mathematical model of the PPG signal, the reference PPG waveform pattern being produced with a reaction-diffusion model, with diastolic and systolic phases of a heart coupled with the reaction and diffusion properties of the reaction-diffusion model;

applying pattern recognition to the first time series with respect to the reference PPG waveform pattern by assigning a recognition score to the waveforms in the first time series, wherein applying the pattern recognition comprises applying cross-correlation analysis between the waveforms in the first time series and the reference PPG waveform pattern; and based on the pattern recognition, producing a resulting PPG signal.

15. The method of claim 14, further comprising bandpass filtering the PPG signal.

16. The method of claim 15, wherein bandpass filtering the PPG signal comprises a joint low-pass and high-pass filtering.

17. The method of claim 14, wherein detecting the peaks and valleys comprises calculating first and second derivatives of the PPG signal.

18. The method of claim 14, further comprising normalizing the PPG signal to a unitary range prior to the segmenting.

19. The method of claim 14, wherein the reference PPG waveform pattern is produced via a self-adaptive nonlinear oscillator.

20. The method of claim 14, wherein the reference PPG waveform pattern is produced with a neural network.

21. The method of claim 14, further comprising resealing the reference PPG waveform pattern over time to facilitate applying pattern recognition to time-comparable waveforms.

22. A method comprising:

receiving a photoplethysmography (PPG) signal collected by a PPG sensing apparatus;

detecting peaks and valleys in the PPG signal;

segmenting the PPG signal to provide a first time series of PPG waveforms located between two subsequent valleys in the PPG signal;

producing a reference PPG waveform pattern based on a mathematical model of the PPG signal, the reference PPG waveform pattern being produced with a reaction-diffusion model, with diastolic and systolic phases of a heart coupled with the reaction and diffusion properties of the reaction-diffusion model;

applying pattern recognition to the first time series with respect to the reference PPG waveform pattern by assigning a recognition score to the waveforms in the first time series, wherein applying the pattern recognition comprises applying cross-correlation analysis between the waveforms in the first time series and the reference PPG waveform pattern, and wherein the recognition score includes a cross-correlation index; and based on the pattern recognition, producing a resulting PPG signal.

* * * * *

UNITED STATES PATENT AND TRADEMARK OFFICE
CERTIFICATE OF CORRECTION

PATENT NO.         : 11,337,617 B2
APPLICATION NO.    : 16/037328
DATED              : May 24, 2022
INVENTOR(S)        : Francesco Rundo et al.

It is certified that error appears in the above-identified patent and that said Letters Patent is hereby corrected as shown below:

In the Claims

Claim 8, Column 22, Line 20; delete "resealing" and insert --rescaling--.

Claim 21, Column 24, Line 1; delete "resealing" and insert --rescaling--.

Signed and Sealed this
Fifth Day of July, 2022

Katherine Kelly Vidal
*Director of the United States Patent and Trademark Office*